US011284781B2

(12) United States Patent
Kuwae et al.

(10) Patent No.: US 11,284,781 B2
(45) Date of Patent: Mar. 29, 2022

(54) ENDOSCOPIC SURGICAL DEVICE AND OVERTUBE

(71) Applicant: FUJIFILM Corporation, Tokyo (JP)

(72) Inventors: Toshiharu Kuwae, Kanagawa (JP); Takumi Dejima, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 357 days.

(21) Appl. No.: 15/710,837

(22) Filed: Sep. 21, 2017

(65) Prior Publication Data
US 2018/0008309 A1 Jan. 11, 2018

Related U.S. Application Data

(63) Continuation of application No. PCT/JP2016/058010, filed on Mar. 14, 2016.
(Continued)

(51) Int. Cl.
*A61B 1/00* (2006.01)
*A61B 17/34* (2006.01)
(Continued)

(52) U.S. Cl.
CPC ...... *A61B 1/00154* (2013.01); *A61B 1/00135* (2013.01); *A61B 1/012* (2013.01);
(Continued)

(58) Field of Classification Search
CPC ............ A61B 1/00131; A61B 1/00133; A61B 1/00135; A61B 1/0014; A61B 1/00154;
(Continued)

(56) References Cited

U.S. PATENT DOCUMENTS 4,566,437 A * 1/1986 Yamaguchi .......... A61B 1/0055
600/131
5,167,220 A * 12/1992 Brown .................... A61B 1/12
600/156
(Continued)

FOREIGN PATENT DOCUMENTS

| WO | 2013176167 | 11/2013 |
| WO | 2014157478 | 10/2014 |
| WO | 2015033905 | 3/2015 |

OTHER PUBLICATIONS

Office Action of Japan Counterpart Application, with English translation thereof, dated Apr. 5, 2019, pp. 1-9.
(Continued)

*Primary Examiner* — Ryan N Henderson
(74) *Attorney, Agent, or Firm* — JCIPRNET

(57) ABSTRACT

This endoscopic surgical device includes: an endoscope; a treatment tool; and a mantle tube. The inside of the mantle tube is partitioned by a partition wall member provided with an endoscope guide groove and a treatment-tool guide groove, to form an endoscope insertion passage and a treatment-tool insertion passage. An endoscope fixation tool and a treatment-tool fixation tool are respectively disposed inside the endoscope guide groove and the treatment-tool guide groove. The endoscope fixation tool advances and retracts in conjunction with the endoscope insertion part inserted through the endoscope insertion passage. The treatment-tool fixation tool moves in conjunction with the treatment-tool insertion part inserted through the treatment-tool insertion passage. When a coupling ring externally fitted to the partition wall member interlocks the endoscope fixation tool with the treatment-tool fixation tool, the endoscope insertion part also moves in conjunction with the advancement and retraction of the treatment-tool insertion part.

11 Claims, 19 Drawing Sheets

Related U.S. Application Data

(60) Provisional application No. 62/136,865, filed on Mar. 23, 2015.

(51) Int. Cl.
*A61B 1/012* (2006.01)
*A61B 17/00* (2006.01)

(52) U.S. Cl.
CPC ........ *A61B 17/00234* (2013.01); *A61B 17/34* (2013.01); *A61B 17/3421* (2013.01); *A61B 2017/0034* (2013.01); *A61B 2017/347* (2013.01); *A61B 2017/3447* (2013.01)

(58) Field of Classification Search
CPC ......... A61B 1/0016; A61B 1/01; A61B 1/313; A61B 1/3132; A61B 17/3423; A61B 17/3427; A61B 17/3429; A61B 2017/347; A61B 2017/3445; A61B 2017/3447
See application file for complete search history.

(56) References Cited

U.S. PATENT DOCUMENTS

| | | | | | |
|---|---|---|---|---|---|
| 5,609,563 | A * | 3/1997 | Suzuki | A61B 1/00098 | 600/107 |
| 5,954,731 | A * | 9/1999 | Yoon | A61B 17/062 | 606/144 |
| 5,993,466 | A * | 11/1999 | Yoon | A61B 17/062 | 606/144 |
| 5,993,467 | A * | 11/1999 | Yoon | A61B 17/0469 | 606/147 |
| 6,126,665 | A * | 10/2000 | Yoon | A61B 17/0469 | 606/144 |
| 7,105,009 | B2 * | 9/2006 | Johnson | A61B 17/3498 | 604/167.03 |
| 7,722,532 | B2 * | 5/2010 | Ikeda | A61B 1/0016 | 600/146 |
| 7,727,255 | B2 * | 6/2010 | Taylor | A61B 17/3423 | 606/205 |
| 7,883,460 | B2 * | 2/2011 | Uchimura | A61B 1/0052 | 600/146 |
| 7,942,834 | B2 * | 5/2011 | Yamada | A61B 1/018 | 601/2 |
| 7,981,028 | B2 * | 7/2011 | Kawai | A61B 1/00055 | 600/145 |
| 8,021,339 | B2 * | 9/2011 | Rockrohr | A61B 17/3498 | 604/167.04 |
| 8,905,973 | B2 * | 12/2014 | Tegg | A61B 17/3498 | 604/167.03 |
| 8,906,014 | B2 * | 12/2014 | Bacher | A61B 17/29 | 606/46 |
| 9,179,933 | B2 * | 11/2015 | Davis | A61B 17/3423 | |
| 9,314,267 | B2 * | 4/2016 | Piskun | A61B 17/3439 | |
| 10,165,933 | B2 * | 1/2019 | Dejima | A61B 1/00135 | |
| 2003/0055437 | A1 * | 3/2003 | Yasunaga | A61B 1/00154 | 606/130 |
| 2004/0073083 | A1 * | 4/2004 | Ikeda | A61B 1/00039 | 600/101 |
| 2004/0167559 | A1 * | 8/2004 | Taylor | A61B 17/3423 | 606/185 |
| 2005/0085774 | A1 * | 4/2005 | Streifinger | A61B 17/3498 | 604/167.01 |
| 2005/0119525 | A1 * | 6/2005 | Takemoto | A61B 1/00137 | 600/114 |
| 2005/0182292 | A1 * | 8/2005 | Suzuki | A61B 1/00137 | 600/104 |
| 2006/0247495 | A1 * | 11/2006 | Bacher | A61B 18/1445 | 600/106 |
| 2007/0049966 | A1 * | 3/2007 | Bonadio | A61B 17/3423 | 606/206 |
| 2007/0265502 | A1 * | 11/2007 | Minosawa | A61B 17/3421 | 600/173 |
| 2008/0033450 | A1 * | 2/2008 | Bayer | A61B 17/3417 | 606/108 |
| 2008/0262296 | A1 * | 10/2008 | Suzuki | A61B 1/00133 | 600/106 |
| 2009/0203961 | A1 * | 8/2009 | Regadas | A61B 1/31 | 600/106 |
| 2009/0227843 | A1 * | 9/2009 | Smith | A61B 17/3423 | 600/208 |
| 2009/0270680 | A1 * | 10/2009 | Takada | A61B 1/31 | 600/118 |
| 2010/0004600 | A1 * | 1/2010 | Rockrohr | A61B 17/3421 | 604/167.04 |
| 2010/0069710 | A1 * | 3/2010 | Yamatani | A61B 1/018 | 600/102 |
| 2010/0081880 | A1 * | 4/2010 | Widenhouse | A61B 1/018 | 600/201 |
| 2010/0113886 | A1 * | 5/2010 | Piskun | A61B 17/0218 | 600/231 |
| 2010/0241082 | A1 * | 9/2010 | Taylor | A61M 39/06 | 604/167.03 |
| 2010/0249516 | A1 * | 9/2010 | Shelton, IV | A61B 17/0293 | 600/203 |
| 2010/0262080 | A1 * | 10/2010 | Shelton, IV | A61B 17/3423 | 604/164.09 |
| 2010/0312063 | A1 * | 12/2010 | Hess | A61B 17/3423 | 600/204 |
| 2011/0082343 | A1 * | 4/2011 | Okoniewski | A61B 17/0293 | 600/208 |
| 2011/0230713 | A1 * | 9/2011 | Kleemann | A61B 1/00165 | 600/106 |
| 2011/0295074 | A1 * | 12/2011 | Stefanchik | A61B 17/3423 | 600/201 |
| 2012/0130177 | A1 * | 5/2012 | Davis | A61B 17/3423 | 600/201 |
| 2012/0232339 | A1 * | 9/2012 | Csiky | A61B 1/00135 | 600/104 |
| 2012/0253132 | A1 * | 10/2012 | Davis | A61B 17/3423 | 600/201 |
| 2012/0253133 | A1 * | 10/2012 | Okoniewski | A61B 1/00135 | 600/201 |
| 2012/0253383 | A1 * | 10/2012 | Russo | A61B 17/3423 | 606/201 |
| 2012/0316391 | A1 * | 12/2012 | Weitzner | A61B 17/00234 | 600/104 |
| 2014/0051934 | A1 * | 2/2014 | Ma | A61B 17/3423 | 600/208 |
| 2014/0100421 | A1 * | 4/2014 | Dejima | A61B 1/00052 | 600/101 |
| 2014/0128671 | A1 * | 5/2014 | Riek | A61B 17/30 | 600/104 |
| 2014/0207070 | A1 * | 7/2014 | Tegg | A61B 17/3498 | 604/167.05 |
| 2014/0275796 | A1 * | 9/2014 | McGrogan | A61B 34/30 | 600/208 |
| 2015/0080650 | A1 * | 3/2015 | Dejima | A61B 17/00234 | 600/102 |
| 2015/0250498 | A1 * | 9/2015 | Kikuchi | A61B 17/3462 | 604/67 |
| 2016/0015256 | A1 | 1/2016 | Iwasaka | | |
| 2016/0113638 | A1 * | 4/2016 | Malkowski | A61B 17/0218 | 606/130 |
| 2016/0175005 | A1 | 6/2016 | Dejima | | |
| 2017/0049474 | A1 * | 2/2017 | Piskun | A61B 17/0218 | |
| 2017/0215919 | A1 * | 8/2017 | Shelton, IV | A61B 17/3431 | |

OTHER PUBLICATIONS

"International Search Report (Form PCT/ISA/210) of PCT/JP2016/058010," dated May 17, 2016, with English translation thereof, pp. 1-4.

"Written Opinion of the International Searching Authority (Form PCT/ISA/237) of PCT/JP2016/051786," dated May 17, 2016, with English translation thereof, pp. 1-14.

(56) References Cited

OTHER PUBLICATIONS

"Written Opinion of the International Searching Authority (Form PCT/ISA/237) of PCT/JP2016/058010," dated May 17, 2016, with English translation thereof, pp. 1-14.
"Office Action of Japan Counterpart Application," dated May 11, 2018, with English translation thereof, p. 1-p. 6.

* cited by examiner

ENDOSCOPIC SURGICAL DEVICE AND OVERTUBE

CROSS-REFERENCE TO RELATED APPLICATIONS

This application is a Continuation of PCT International Application No. PCT/JP2016/058010 filed on Mar. 14, 2016, which claims priority under 35 U.S.C. § 119(a) to U.S. Provisional Application No. 62/136,865 filed on Mar. 23, 2015. Each of the above applications is hereby expressly incorporated by reference, in their entirety, into the present application.

BACKGROUND OF THE INVENTION

1. Field of the Invention

The present invention relates to an endoscopic surgical device and an overtube, and particularly, relates to an endoscopic surgical device and an overtube that can operate an endoscope and a treatment tool inserted through two insertion passages provided in an overtube in an interlocking manner.

2. Description of the Related Art

In recent years, since invasion to a patient is small compared to surgery in which a laparotomy, a thoracotomy, or the like is performed, endoscopic surgery using endoscopes (hard endoscopes), such as a laparoscope, is widely performed. In the endoscopic surgery, a plurality of holes are made in a patient's body wall, an endoscope is inserted into a body cavity from one hole of them, and a treatment tool is inserted into the body cavity from another hole. Then, treatment of living body tissue is performed with the treatment tool while observing the living body tissue within the body cavity with the endoscope.

Generally, in the endoscopic surgery, one or a plurality of treatment tools are used simultaneously with the endoscope. Therefore, since it is difficult for one operator to simultaneously operate the endoscope and the plurality of treatment tools, for example, a task of operating treatment tools using both hands by the operator while making an assistant called an endoscopic technician operate the endoscope is normally performed.

In this way, in the endoscopic surgery, it is general that the operator's hands are bound by the operation of the treatment tool, and the operation of the endoscope is performed by the assistant. Therefore, in a case where the observation position of the endoscope is changed, the operator should serially give instructions to the assistant. Hence, the task of correctly directing the orientation of the endoscope to a direction desired by the operator is difficult, and stress is likely to be imposed on the operator. Additionally, since the assistant performs an operation after the operator issues an instruction, there is a tendency that surgery time is likely to be prolonged. Additionally, the assistant should operate the endoscope so as not to interfere with an operator's procedure, and the operation is likely to become complicated.

In contrast, the applicant of the present application suggests a technique in which an endoscope and a treatment tool are combined together by an overtube, and if the treatment tool is moved forward and backward, the endoscope is also moved forward and backward in an interlocking manner with this movement of the treatment tool (refer to WO2013/176167A). Specifically, the overtube that guides an insertion part of the endoscope and an insertion part of the treatment tool into a body cavity includes a tubular overtube body that has an endoscope insertion passage and a treatment tool insertion passage through which the insertion part of the endoscope and the insertion part of the treatment tool are inserted, respectively.

A coupling mechanism, which has coupling parts that are respectively coupled to the insertion part of the endoscope and the insertion part of the treatment tool and which is movable forward and backward in an axial direction, is provided inside the overtube body. If the insertion part of the treatment tool is moved forward and backward in the axial direction by the coupling mechanism, the insertion part of the endoscope also moves forward and backward in the axial direction in an interlocking manner with this.

By virtue of such an overtube, the number of holes made in the patient's body wall can be reduced, the invasion to the patient can be suppressed, and the visual field of the endoscope can be easily changed while an operator operates the treatment tool without asking for an assistant's help.

SUMMARY OF THE INVENTION

Meanwhile, in the technique suggested in WO2013/176167A by the applicant of the present application, the above coupling mechanism is disposed inside the overtube body, and a constituent member of the coupling mechanism which integrally moves forward and backward reaches the endoscope insertion passage, the treatment tool insertion passage, and a region between these insertion passages. Therefore, no partition wall member is provided between the endoscope insertion passage and the treatment tool insertion passage.

For that reason, in a case where the endoscope or the treatment tool is inserted through the overtube body, it is necessary to pay attention so that these endoscope and treatment tool do not proceed to any regions other than their original insertion passages inside the overtube body. For that reason, there is a problem that the task of coupling the endoscope or the treatment tool to the coupling mechanism to insert the endoscope or the treatment tool through the overtube requires time and effort.

The invention has been made in view of such circumstances, and an object thereof is to provide an endoscopic surgical device capable of easily inserting medical instruments through an overtube, and the overtube.

In order to achieve the above object, an endoscopic surgical device according to an aspect of the invention is an endoscopic surgical device comprising a first medical instrument having a first insertion part inserted into a body cavity; a second medical instrument having a second insertion part inserted into the body cavity; and an overtube that passes through a body wall, is inserted into the body cavity, and guides the first insertion part and the second insertion part into the body cavity. The overtube includes an overtube body having a distal end, a proximal end, and a longitudinal axis, a first distal end opening and a second distal end opening provided at a distal end of the overtube body, a first proximal end opening and a second proximal end opening provided at a proximal end of the overtube body, a first insertion passage that is provided along the longitudinal axis of the overtube body, allows the first distal end opening and the first proximal end opening to communicate with each other, and allows the first insertion part to be inserted therethrough so as to be movable forward and backward, a second insertion passage that is provided along the longitudinal axis of the overtube body, allows the second distal end opening and the second proximal end opening to communicate with each other, and allows the second insertion part to be inserted therethrough so as to be movable forward and backward, and a coupling mechanism that has a first coupling part coupled to the first insertion part inserted through the first insertion passage and a second coupling part coupled to the second insertion part inserted through the second insertion passage. The coupling mechanism includes a partition wall member that is housed inside the overtube body and extends along the longitudinal axis and that has a partition wall between the first insertion passage and the second insertion passage, a first fixing tool that has the first coupling part and is movable forward and backward along the first insertion passage, a second fixing tool that has the second coupling part and is movable forward and backward along the second insertion passage, and a ring-shaped driving member that is externally fitted to an outer peripheral part of the partition wall member and is movable forward and backward along the longitudinal axis with respect to the partition wall member and that has a sensing region where either the first fixing tool or the second fixing tool is moved forward and backward in an interlocking manner with the forward and backward movement of the other of the first fixing tool and the second fixing tool.

According to this aspect, since the partition wall member having the a partition wall between the first insertion passage and the second insertion passage is included as the coupling mechanism, in a case where the first medical instrument or the second medical instrument is inserted through the first insertion passage or the second insertion passage, the medical instruments can be restrained from proceeding to regions other than the respective insertion passages.

Accordingly, if an operator inserts the first medical instrument and the second medical instrument into the overtube, the medical instruments reliably proceed to their corresponding insertion passages and are reliably coupled to their corresponding fixing tools. Hence, the task of inserting the medical instruments into the overtube becomes easy.

In the endoscopic surgical device according to another aspect of the invention, it is possible to adopt an aspect in which the driving member further has a non-sensing region where either the first fixing tool or the second fixing tool is not moved forward and backward in an interlocking manner with the forward and backward movement of the other of the first fixing tool and the second fixing tool.

According to this aspect, the non-sensing region where either the first medical instrument or the second medical instrument is not moved forward and backward with the forward and backward movement of the other of the first medical instrument and the second medical instrument in the axial direction.

In the endoscopic surgical device according to still another aspect of the invention, it is possible to adopt an aspect in which the driving member has a first engaging part engaged with the first fixing tool and a second engaging part engaged with the second fixing tool, the first engaging part has a first restricting part that restricts the forward and backward movement of the first fixing tool in a first range, and the second engaging part has a second restricting part that restricts the forward and backward movement of the second fixing tool in a second range different from the first range.

According to the present aspect, both of the first fixing tool and the second fixing tool are configured separately from the driving member. Also, the first fixing tool and the second fixing tool are respectively engaged with the first engaging part and the second engaging part of the driving member, and the movement range where the forward and backward movement is possible with respect to the driving member is restricted by the engaging parts.

In the endoscopic surgical device according to a still further aspect of the invention, it is possible to adopt an aspect in which the driving member has a first engaging part engaged with the first fixing tool and a second engaging part engaged with the second fixing tool, and at least one of the first engaging part or the second engaging part allows the movement of a corresponding fixing tool in a direction along with the longitudinal axis.

According to the present aspect, both of the first fixing tool and the second fixing tool are configured separately from the driving member. Also, the first fixing tool and the second fixing tool are respectively engaged with the first engaging part and the second engaging part of the driving member, and the movement range where the forward and backward movement is possible with respect to the driving member is restricted by the engaging parts. This aspect has the movement range where the forward and backward movement of at least one of the first fixing tool and the second fixing tool with respect to the driving member is allowed.

In the endoscopic surgical device according to a still further aspect of the invention, it is possible to adopt an aspect in which the driving member has a first engaging part engaged with the first fixing tool and a second engaging part engaged with the second fixing tool, and at least one of the first engaging part or the second engaging part allows the rotation of a corresponding fixing tool in a direction around an axis.

According to the present aspect, both of the first fixing tool and the second fixing tool are configured separately from the driving member. Also, the first fixing tool and the second fixing tool are respectively engaged with the first engaging part and the second engaging part of the driving member, and the movement range where forward and backward movement is possible with respect to the driving member is restricted by the engaging parts. In this aspect, at least one of the first fixing tool and the second fixing tool moves in the circumferential direction.

In the endoscopic surgical device according to a still further aspect of the invention, it is possible to adopt an aspect in which the partition wall member has a first guide groove that constitutes a portion of the first insertion passage, and a second guide groove that constitutes a portion of the second insertion passage.

In the endoscopic surgical device according to a still further aspect of the invention, it is possible to adopt an aspect in which the first insertion passage and the second insertion passage are disposed parallel to each other.

In the endoscopic surgical device according to a still further aspect of the invention, it is possible to adopt an aspect in which the first insertion passage and the second insertion passage are disposed to obliquely intersect each other.

In the endoscopic surgical device related to a still further aspect of the invention, it is possible to adopt an aspect in which the first medical instrument is an endoscope in which an observation part is provided at a distal end of the first insertion part, and the second medical instrument is a treatment tool in which a treatment part is provided at a distal end of the second insertion part.

In the endoscopic surgical device related to a still further aspect of the invention, it is possible to adopt an aspect in which the first medical instrument is an endoscope in which an observation part is provided at a distal end of the first insertion part, the second medical instrument is a treatment tool in which a treatment part is provided at a distal end of the second insertion part, the first insertion passage is disposed to obliquely intersect the longitudinal axis of the overtube body, and the second insertion passage is disposed parallel to the longitudinal axis of the overtube body.

An overtube according to an aspect of the invention is an overtube comprising an overtube body having a distal end, a proximal end, and a longitudinal axis; a first distal end opening and a second distal end opening provided at a distal end of the overtube body; a first proximal end opening and a second proximal end opening provided at a proximal end of the overtube body, a first insertion passage that is provided along the longitudinal axis of the overtube body, allows the first distal end opening and the first proximal end opening to communicate with each other, and allows a first insertion part of a first medical instrument to be inserted therethrough so as to be movable forward and backward; a second insertion passage that is provided along the longitudinal axis of the overtube body, allows the second distal end opening and the second proximal end opening to communicate with each other, and allows a second insertion part of a second medical instrument to be inserted therethrough so as to be movable forward and backward; and a coupling mechanism that has a first coupling part coupled to the first insertion part inserted through the first insertion passage and a second coupling part coupled to the second insertion part inserted through the second insertion passage. The coupling mechanism includes a partition wall member that is housed inside the overtube body and extends along the longitudinal axis and that has a partition wall between the first insertion passage and the second insertion passage, a first fixing tool that has the first coupling part and is movable forward and backward along the first insertion passage, a second fixing tool that has the second coupling part and is movable forward and backward along the second insertion passage, and a ring-shaped driving member that is externally fitted to an outer peripheral part of the partition wall member and is movable forward and backward along the longitudinal axis with respect to the partition wall member and that has a sensing region where either the first fixing tool or the second fixing tool is moved forward and backward in an interlocking manner with the forward and backward movement of the other of the first fixing tool and the second fixing tool.

According to this aspect, since the partition wall member having the partition wall between the first insertion passage and the second insertion passage is included as the coupling mechanism, in a case where the first medical instrument or the second medical instrument is inserted through the first insertion passage or the second insertion passage, the medical instruments can be restrained from proceeding to regions other than the respective insertion passages.

Accordingly, the first medical instrument reliably proceeds through the first insertion passage, the second medical instrument reliably proceeds through the second insertion passage, and these medical instruments are also reliably coupled to the coupling mechanism and inserted through the overtube. Hence, the task of inserting the medical instruments into the overtube becomes easy.

According to the invention, the medical instruments can be easily inserted through the overtube.

DESCRIPTION OF THE PREFERRED EMBODIMENTS

Preferred embodiments of the invention will be described below in detail according to the accompanying drawings. In addition, any of the drawings may illustrate main parts in an exaggerated manner for description, and may have dimensions different from actual dimensions.

Figure 1:
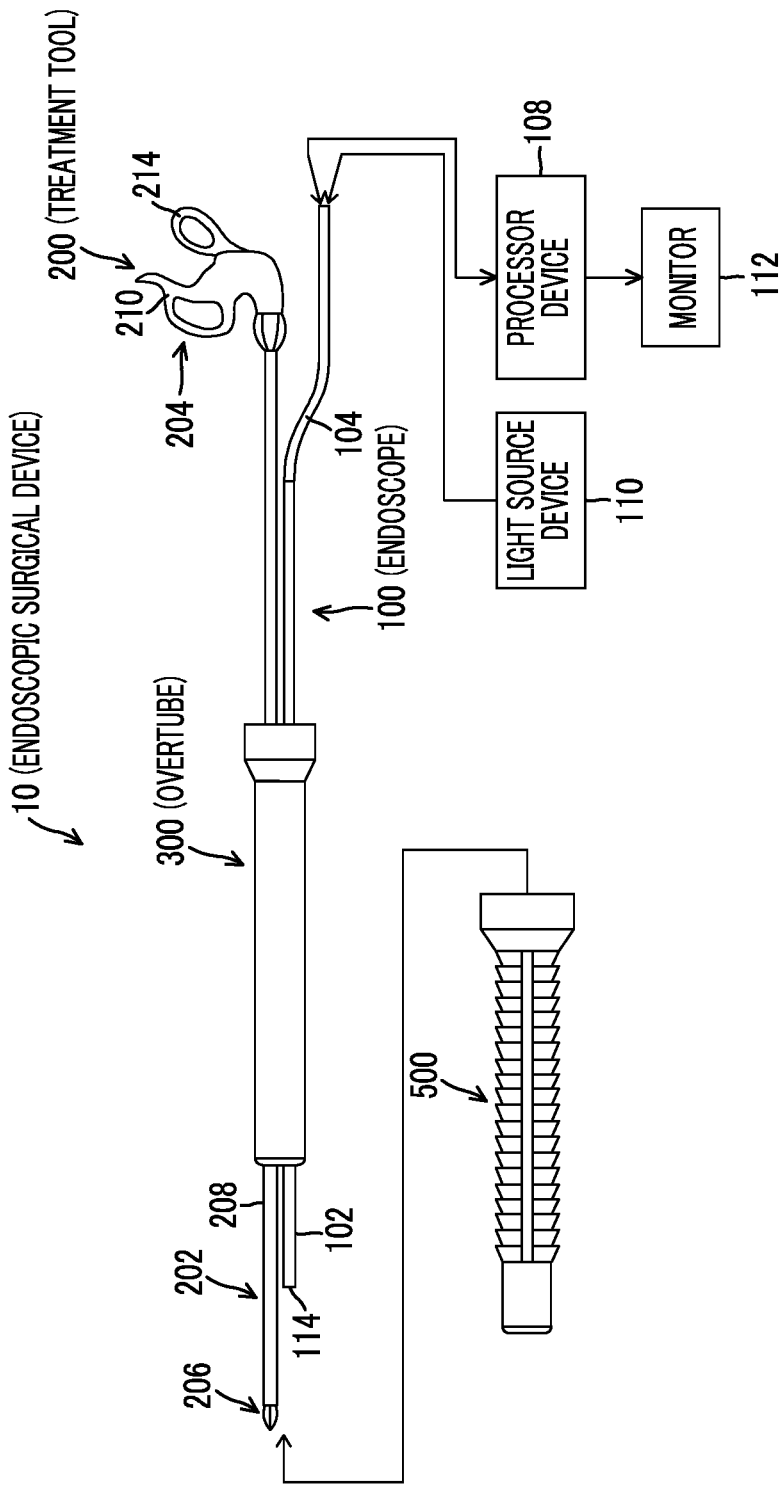
FIG. 1 is a schematic block diagram of an endoscopic surgical device according to the invention.

FIG. 1 is a schematic block diagram of an endoscopic surgical device according to the invention. As illustrated in FIG. 1, an endoscopic surgical device 10 includes an endoscope 100 that is one form of a first medical instrument having a first insertion part inserted into a body cavity and observes the inside of a patient's body cavity, a treatment tool 200 that is one form of a second medical instrument having a second insertion part inserted into the body cavity and examines or treats a diseased site within the patient's body cavity, an overtube 300 that is inserted into the body cavity through a body wall and guides an insertion part 102 of the endoscope 100, which is a first insertion part, and an insertion part 202 of a treatment tool 200, which is a second insertion part, to the inside of the body cavity, and a sheathing tube 500 fitted to the overtube 300.

The endoscope 100 is, for example, a hard endoscope, such as a laparoscope, and includes an insertion part 102 (hereinafter referred to as "endoscope insertion part 102") that is inserted into a body cavity, and that has an outer peripheral part surrounded by an elongated hard tubular body, and a cable part 104 that is consecutively installed on a proximal end side of the endoscope insertion part 102 and that has an outer peripheral part surrounded by an elongated flexible tubular body.

The cable part 104 indicates a flexible cable portion in which a wire rod, such as a cable or a light guide, which extends from a proximal end of the endoscope insertion part 102, is housed by covering the wire rod with, for example, a flexible insulating member, such as polyvinyl chloride.

A connector (not illustrated) is provided at an end of the cable part 104 on its extension destination, and each of a processor device 108 that is a control device and a light source device 110 is detachably connected to the cable part via the connector. Additionally, the processor device 108 is connected to a monitor 112 via a cable.

Figure 2:
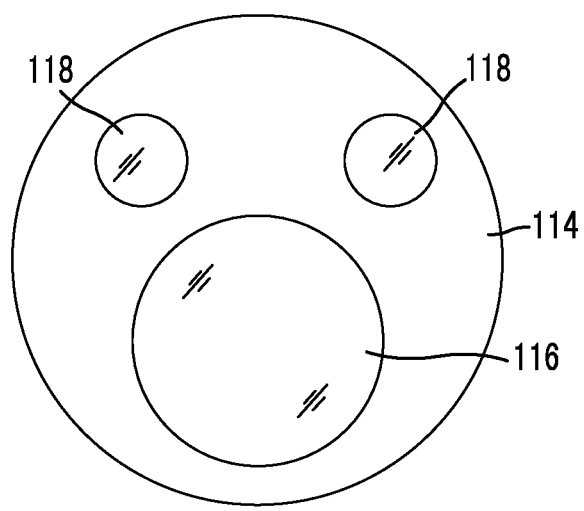
FIG. 2 is a plan view illustrating a distal end surface of the endoscope insertion part.

As illustrated in FIG. 2, a distal end surface 114 of the endoscope insertion part 102 is provided with an observation window 116 and illumination windows 118 and 118.

A distal end of the endoscope insertion part 102 is provided with an observation part, and an observation window 116 is provided as a constituent element of the observation part. Additionally, as constituent elements of the observation part, and an objective lens of an observation optical system, and a solid image pickup element, such as a charge coupled device (CCD) image sensor or a complementary metal oxide semiconductor (CMOS) image sensor, which is disposed at an image pickup position of the objective lens, are disposed behind the observation window 116.

A signal cable (not illustrated) connected to this solid image pickup element is inserted through the endoscope insertion part 102 and the cable part 104 of FIG. 1, is provided to extend up to the connector (not illustrated), and is connected to the processor device 108. An observation image picked up from the observation window 116 is formed on a light-receiving surface of the image pickup element, and is converted into electrical signals (image pickup signals), and the electrical signals are output to the processor device 108 via the signal cable and are converted into video signals. Then, the video signals are output to the monitor 112 connected to the processor device 108, and the observation image (endoscopic image) is displayed on a screen of the monitor 112.

An emission end of the light guide (not illustrated) is disposed behind the illumination windows 118 and 118 of FIG. 2 to constitute an illumination part. The light guide is inserted through the endoscope insertion part 102 and the cable part 104 of FIG. 1 and has an incident end disposed within the connector (not illustrated). Hence, by coupling the connector to the light source device 110, the illumination light radiated from the light source device 110 is transmitted to the illumination windows 118 and 118 via the light guide, and is radiated forward from the illumination windows 118 and 118. In addition, in FIG. 2, the two illumination windows 118 and 118 are disposed on the distal end surface 114 of the endoscope insertion part 102. However, the number of illumination windows 118 is not limited, and the number thereof may be one or may be three or more. Additionally, the endoscope 100 may not include the illumination part.

As illustrated in FIG. 1, the treatment tool 200 consists of, for example, forceps, and includes an elongated insertion part 202 (hereinafter referred to as a "treatment tool insertion part 202") that is inserted into a body cavity, an operating part 204 that is provided on the proximal end side of the treatment tool insertion part 202 and is gripped by an operator, and a treatment part 206 that is provided at a distal end of the treatment tool insertion part 202 and is operable by the operation of the operating part 204.

The treatment tool insertion part 202 is provided with a tubular sheath 208, and an operating shaft (not illustrated) that is inserted into the sheath 208 so as to be movable in the direction of an axial center. Moreover, the operating part 204 is provided with a fixed handle 210, and a movable handle 214 that is coupled to the fixed handle 210 in a rotationally movable manner via a rotational movement pin. A proximal end part of the operating shaft is coupled to the movable handle 214.

The treatment part 206 is provided with a pair of gripping members that is openable and closable. The gripping members are coupled to a distal end part of the operating shaft via a driving mechanism (not illustrated). With the rotational movement operation of the movable handle 214 of the operating part 204, the gripping members of the treatment part 206 are opened and closed via the operating shaft and the driving mechanism.

In addition, the treatment tool 200 is not limited to the forceps, and may be, for example, other treatment tools, such as a laser probe, a suture device, an electric scalpel, a needle holder, an ultrasonic device, and an aspirator.

As illustrated in FIG. 1, the overtube 300 allows the endoscope insertion part 102 and the treatment tool insertion part 202, which are inserted thereinto from the proximal end side, to be inserted therethrough and delivered from the distal end side. By inserting the overtube 300 into a body wall and having a proximal end side thereof disposed outside of the body and a distal end side thereof disposed within the body cavity, the endoscope insertion part 102 and the treatment tool insertion part 202 are guided into the body cavity with one overtube 300. Additionally, the overtube 300 includes an interlocking function of moving the endoscope insertion part 102 and the treatment tool insertion part 202 forward and backward in an interlocking manner as will be described below in detail. For example, the endoscope insertion part 102 can also be moved forward and backward by the forward and backward movement operation of only the treatment tool insertion part 202, and a suitable endoscopic image can be obtained without performing the forward and backward movement operation of the endoscope insertion part 102. The details of the configuration and working of the overtube 300 will be described below.

Figure 3:
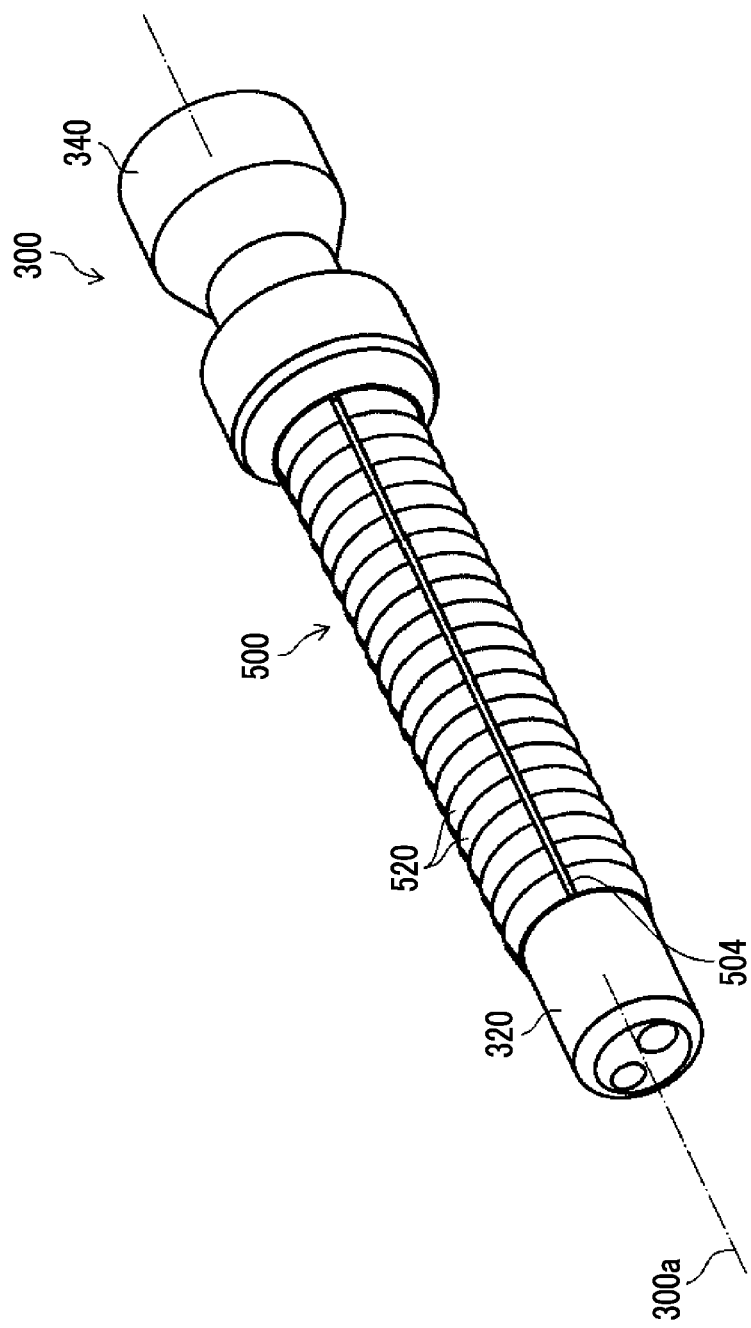
FIG. 3 is a perspective view illustrating a state where a sheathing tube is fitted to the overtube.

The sheathing tube 500 illustrated in FIG. 1 is formed in a tubular shape, and as illustrated in FIG. 3, is externally fitted (sheathed) to and fixed to an outer peripheral surface of the overtube 300 (a long tubular overtube part 320 to be described below). Although detailed description is omitted, an outer peripheral part of the sheathing tube 500 is provided with a number of lateral grooves 520 running along in a circumferential direction, and four longitudinal grooves 504 running along an axial direction are provided, for example, in four places in the circumferential direction.

Accordingly, in a state where the overtube 300 is inserted into a body wall together with the sheathing tube 500, a number of the lateral grooves 520 of the sheathing tube 500 restrict the forward and backward movement of the sheathing tube 500 with respect to the body wall, and the longitudinal grooves in four places of the sheathing tube 500 restrict the rotation of the sheathing tube 500 in the circumferential direction (around a reference axis 300a) with respect to the body wall. Hence, unintended rotation or forward and backward movement of the overtube 300 fixed to the sheathing tube 500 with respect to the body wall is prevented.

Namely, if the overtube 300 rotates in a direction around the axis with respect to the reference axis 300a that is a central axis (longitudinal axis) of the overtube 300 unintentionally with respect to the body wall or moves forward and backward in the direction (axial direction) of the reference axis 300a in a case where the operation of the treatment tool 200, or the like is performed by inserting the endoscope insertion part 102 and the treatment tool insertion part 202 through the overtube 300 after the overtube 300 (long tubular overtube part 320) is inserted into the body wall, there is a problem that the position of a distal end of the endoscope insertion part 102 may fluctuate and an observation visual field may fluctuate unintentionally. The sheathing tube 500 prevents such unintended fluctuation of the observation visual field.

Figure 4:
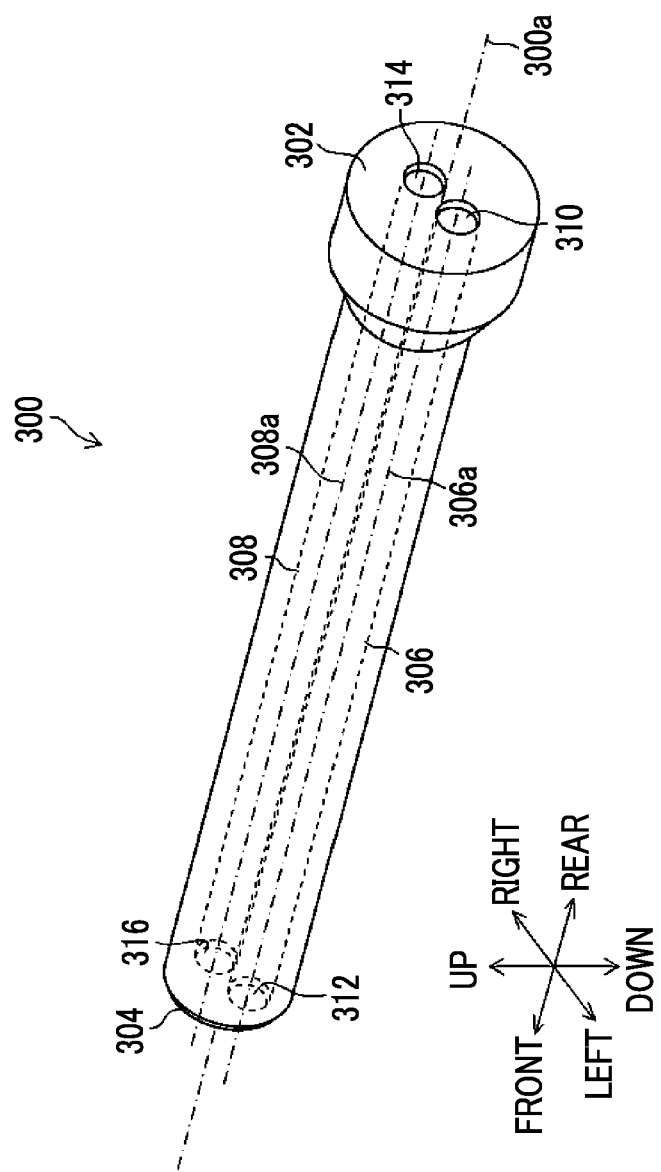
FIG. 4 is an external perspective view illustrating the overtube.

FIG. 4 is an external perspective view illustrating the overtube 300.

As illustrated in this drawing, the overtube 300 has an elongated cylindrical shape as a whole, and has an endoscope insertion passage 306 through which the endoscope insertion part 102 of the endoscope 100 is inserted so as to be movable forward and backward along the reference axis 300a indicating a longitudinal axis thereof, and a treatment tool insertion passage 308 through which the treatment tool insertion part 202 of the treatment tool 200 is inserted so as to be movable forward and backward along the reference axis 300a indicating a longitudinal axis thereof. The endoscope insertion passage 306 is one form of a first insertion passage through which the first insertion part of the first medical instrument is inserted so as to be movable forward and backward, and the treatment tool insertion passage 308 is one form of a second insertion passage through which the second insertion part of the second medical instrument is inserted so as to so as to be movable forward and backward.

Additionally, the endoscope insertion passage 306 and the treatment tool insertion passage 308 are disposed parallel to each other and are disposed parallel to the reference axis 300a. That is, in a case where a central axis of the endoscope insertion passage 306 is referred to as an endoscope insertion axis 306a and a central axis of the treatment tool insertion passage 308 is referred to as a treatment tool insertion axis 308a, the endoscope insertion axis 306a and the treatment tool insertion axis 308a are parallel to each other and are also parallel to the reference axis 300a. The endoscope insertion axes 306a and the treatment tool insertion axes 308a are equivalent to positions of the central axes of the endoscope insertion part 102 and the treatment tool insertion part 202 that are respectively inserted through the endoscope insertion passage 306 and the treatment tool insertion passage 308. Additionally, in the present embodiment, the reference axis 300a, the endoscope insertion axis 306a, and the treatment tool insertion axis 308a are disposed on the same plane. However, a configuration in which the reference axis 300a, the endoscope insertion axis 306a, and the treatment tool insertion axis 308a are disposed on the same plane may not be adopted.

In addition, regarding the position and orientation of a space where the overtube 300 has been disposed, terms called forward, backward, left, right, up, and down are used with the orientation from the proximal end surface 302 in a direction along the reference axis 300a to the distal end surface 304 defined as the forward and with the orientation from the reference axis 300a to the treatment tool insertion axis 308a defined as the right.

The proximal end surface 302 of the overtube 300 is provided with a first proximal end opening 310 that is a proximal end opening that allows the endoscope insertion part 102 to be inserted into the endoscope insertion passage 306 therethrough, and a second proximal end opening 314 that is a proximal end opening that allows the treatment tool insertion part 202 to be inserted into the treatment tool insertion passage 308 therethrough.

The distal end surface 304 of the overtube 300 is provided with a first distal end opening 312 that is a distal end opening that allows the endoscope insertion part 102 to be inserted into the endoscope insertion passage 306 and delivered to the outside therethrough, and a second distal end opening 316 that is a distal end opening that allows the treatment tool insertion part 202 to be inserted into the treatment tool insertion passage 308 and delivered to the outside therethrough.

That is, the endoscope insertion passage 306 that is one form of the first insertion passage allows the first distal end opening 312 and the first proximal end opening 310 to communicate with each other, and the treatment tool insertion passage 308 that is one form of the second insertion passage is provided so as to allow the second distal end opening 316 and the second proximal end opening 314 to communicate with each other.

Figure 5:
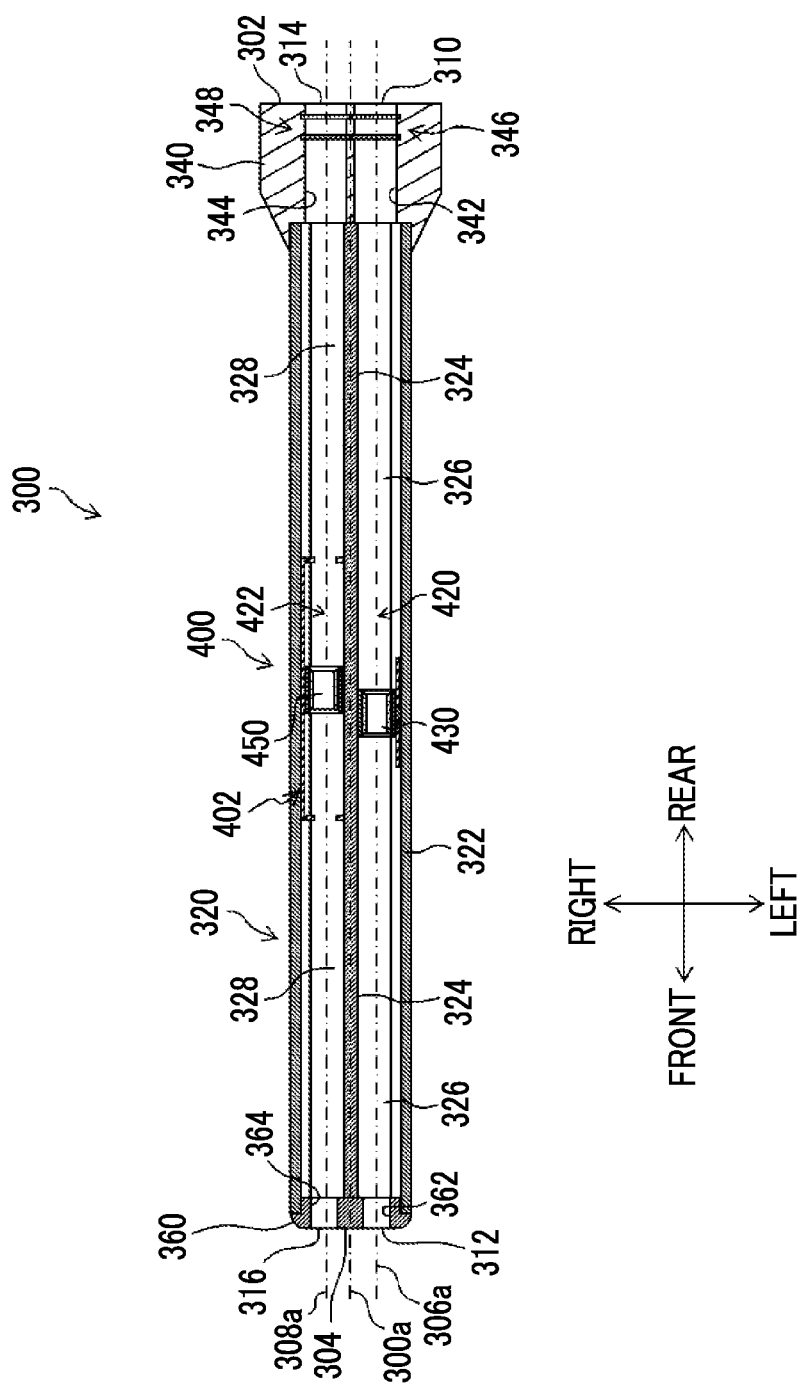
FIG. 5 is a horizontal cross-sectional view illustrating the internal structure of the overtube.

FIG. 5 is a cross-sectional view illustrating the internal structure of the overtube 300, and illustrates a cross section obtained by cutting the overtube 300 in a plane (horizontal plane) that includes the reference axis 300a and is orthogonal to an upward-downward direction.

As illustrated in this drawing, the overtube 300 is constituted by a long tubular overtube part 320 that occupies portions other than a proximal end portion and a distal end portion, a proximal end cap 340 that is attached to a rear end (proximal end) of the overtube 300, and a distal end cap 360 that is attached to a distal end part.

Additionally, the long tubular overtube part 320 is constituted by a long tubular body 322 formed in an elongated cylindrical shape having the reference axis 300a as a central axis (longitudinal axis) using hard resin, metal, or the like, a columnar partition wall member 324 that is housed and disposed inside the long tubular body 322 and extends along the reference axis 300a and that has an endoscope guide groove 326 and a treatment tool guide groove 328 that respectively form portions of the endoscope insertion passage 306 and the treatment tool insertion passage 308, and a slider 400 that is guided by the partition wall member 324 and supported to be movable forward and backward in the forward-backward direction. The details regarding the partition wall member 324 and the slider 400 will be described below.

The proximal end cap 340 is formed in a columnar shape of which the diameter is made larger than the external diameter of the long tubular overtube part 320 (cylindrical body) using hard resins, metals, or the like, and a rear end surface thereof constitutes the proximal end surface 302 of the overtube 300. The proximal end cap 340 is provided with a through-hole 342 and a through-hole 344 that form a portion of the endoscope insertion passage 306 and a portion of the treatment tool insertion passage 308, respectively, and through-holes 342 and 344 respectively communicate with the endoscope guide groove 326 and the treatment tool guide groove 328 of the long tubular overtube part 320. In the proximal end surface 302, an opening of the through-hole 342 is equivalent to the above-described first proximal end opening 310, and an opening of the through-hole 344 is equivalent to the above-described second proximal end opening 314.

Additionally, the through-holes 342 and 344 are provided with valve members 346 and 348. The valve members 346 and 348, for example, open in a case where the endoscope insertion part 102 and the treatment tool insertion part 202 are inserted therethrough and come into close contact with outer peripheral surfaces (side surfaces) of the endoscope insertion part 102 and the treatment tool insertion part 202 without a substantial gap. This secures the airtightness of spaces closer to the distal end side than the valve members 346 and 348, and reduces the leakage or the like of a pneumoperitoneum gas injected into the body cavity to the outside of the body.

The distal end cap 360 is formed of hard resins, metals, or the like, and a front end surface thereof constitutes the distal end surface 304 of the overtube 300. The distal end cap 360 is provided with a through-hole 362 and a through-hole 364 that form a portion of the endoscope insertion passage 306 and a portion of the treatment tool insertion passage 308, respectively, and through-holes 362 and 364 respectively communicate with the endoscope guide groove 326 and the treatment tool guide groove 328 of the long tubular overtube part 320. In the distal end surface 304, an opening of the through-hole 362 is equivalent to the above-described first distal end opening 312, and an opening of the through-hole 364 is equivalent to the second distal end opening 316.

In addition, the long tubular overtube part 320, the proximal end cap 340, and the distal end cap 360 show one form of constituent members that constitutes the overtube body of the overtube 300, and the overtube body is not limited to the above configuration. For example, the long tubular overtube part 320 and the proximal end cap 340 or the long tubular overtube part 320 and the distal end cap 360 may be integrally formed, or may be integrally formed in their entirety.

The partition wall member 324 and the slider 400 in the above-described long tubular overtube part 320 constitute a coupling mechanism having a first coupling part coupled to the first insertion part of the first medical instrument inserted through the first insertion passage, and a second coupling part coupled to the second insertion part of the second medical instrument inserted through the second insertion passage.

Figure 6:
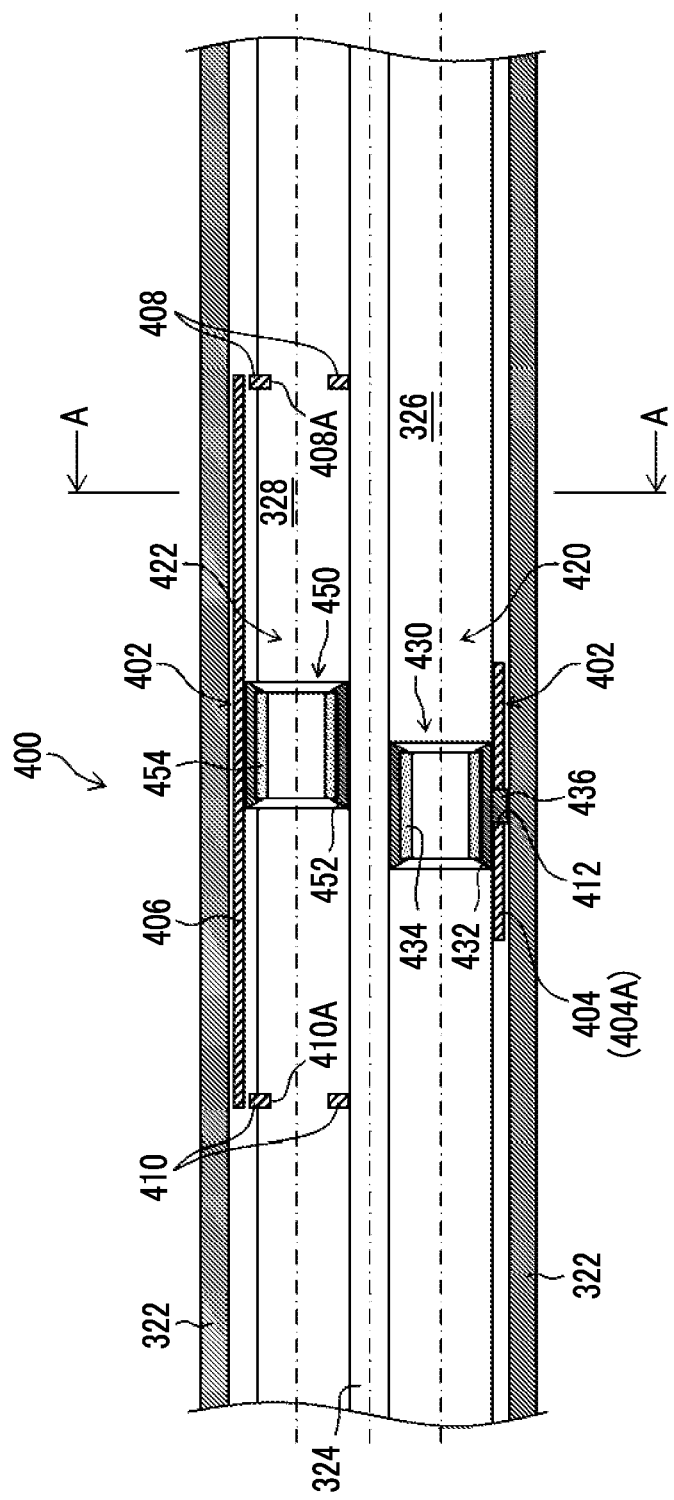
FIG. 6 is an enlarged view of a portion where the slider is disposed in FIG. 5.
Figure 7:
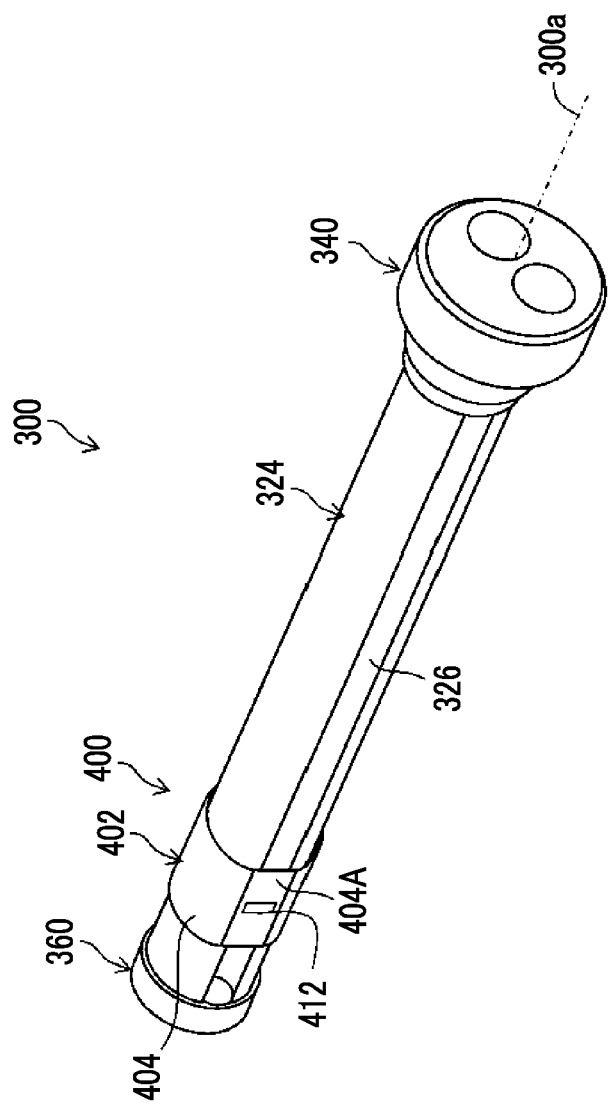
FIG. 7 is a perspective view illustrating the overtube with a long tubular body in a long tubular overtube part omitted.
Figure 8:
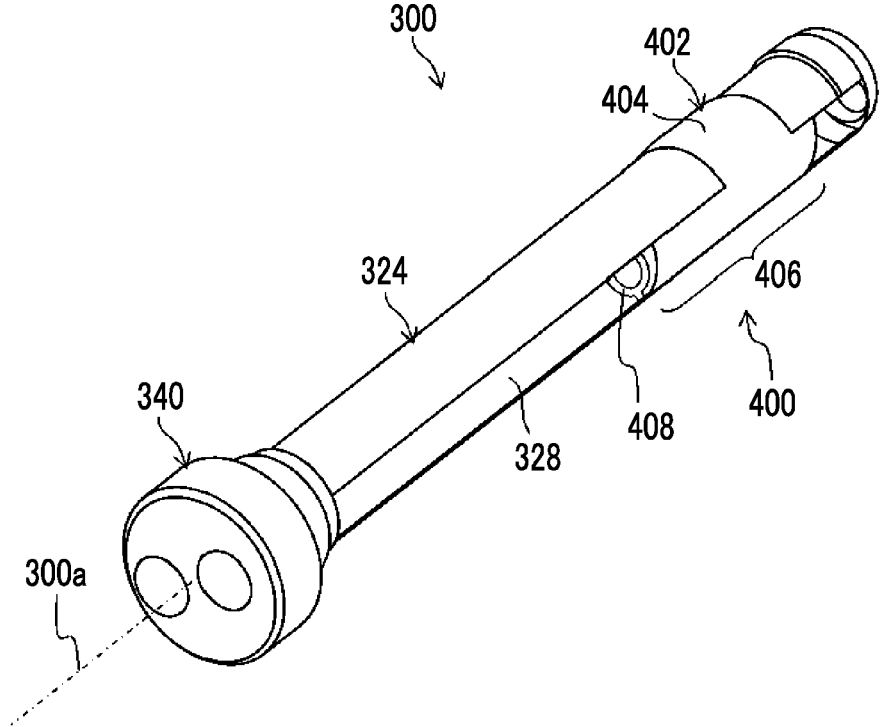
FIG. 8 is a perspective view illustrating the overtube with the long tubular body in the long tubular overtube part omitted.

FIG. 6 is a partially enlarged view illustrating a portion, in which the slider 400 is disposed in FIG. 5, in an extracted manner, and FIGS. 7 and 8 are perspective views illustrating the overtube 300 from left and right different directions on the proximal end side with the long tubular body 322 in the long tubular overtube part 320 omitted. As illustrated in these drawings, the slider 400 is supported by the columnar partition wall member 324 having the endoscope guide groove 326 and the treatment tool guide groove 328 inside the long tubular body 322.

Figure 9:
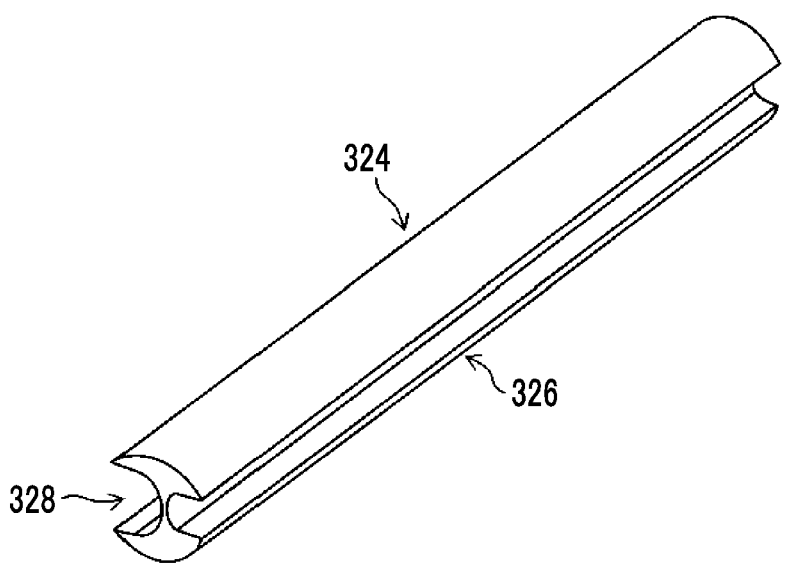
FIG. 9 is a perspective view illustrating only a partition wall member.

The partition wall member 324 is a solid insulator, has a structure as illustrated in FIG. 9, and extends from the proximal end cap 340 to the distal end cap 360 inside the long tubular body 322.

The endoscope guide groove 326, which forms a portion of the endoscope insertion passage 306 and extends parallel to the reference axis 300a from a proximal end of the partition wall member 324 to a distal end thereof, is formed on a left side of the partition wall member 324. The treatment tool guide groove 328, which forms a portion of the treatment tool insertion passage 308 and extends parallel to the reference axis 300a from the proximal end of the partition wall member 324 to the distal end thereof, is formed on a right side of the partition wall member 324.

That is, the partition wall member 324 has the endoscope guide groove 326 as one form of a first guide groove that constitutes a portion of the first insertion passage, and has the treatment tool guide groove 328 as one form of a second guide groove that constitutes a portion of the second insertion passage. Additionally, the partition wall member 324 forms a partition wall between the first insertion passage and the second insertion passage.

By virtue of the partition wall member 324, the endoscope insertion part 102 and the treatment tool insertion part 202 inserted into the overtube 300 reliably proceed through the regions of the endoscope insertion passage 306 and the treatment tool insertion passage 308 corresponding thereto without falling out of the insertion passages, respectively. As a result, the insertion task of the endoscope insertion part 102 with respect to the overtube 300 and the treatment tool insertion part 202 becomes easy.

Additionally, the endoscope insertion part 102 inserted through the endoscope insertion passage 306 and the treatment tool insertion part 202 inserted through the treatment tool insertion passage 308 are prevented from coming into contact with each other inside then overtube 300, and are electrically insulated from each other. For that reason, even in a case where the treatment tool 200 uses electricity, generation of electrical leakage (high-frequency electricity or the like) from the treatment tool 200 to the endoscope 100, electrical noise, or the like can be prevented, and damage or the like to the endoscope 100 can be prevented in advance.

In addition, the partition wall member 324 may act as at least a member that forms a partition wall between the endoscope insertion passage 306 (first insertion passage) and the treatment tool insertion passage 308 (second insertion passage), may not be necessarily formed on the basis of a columnar shape, and may not occupy substantially all regions other than the endoscope insertion passage 306 and treatment tool insertion passage 308 as in the present embodiment.

As illustrated in FIGS. 6, 7, and 8, the slider 400 is a ring-shaped driving member that is externally fitted to an outer peripheral part of the partition wall member 324 and is movable forward and backward along the reference axis 300a with respect to the partition wall member 324, and has a coupling ring 402 that integrally interlocks components of the slider 400, an endoscope fixing tool 430 disposed as a first fixing tool inside the endoscope guide groove 326 of the partition wall member 324 as illustrated in FIG. 6, and a treatment tool fixing tool 450 disposed as a second fixing tool inside the treatment tool guide groove 328 of the partition wall member 324.

Figure 10:
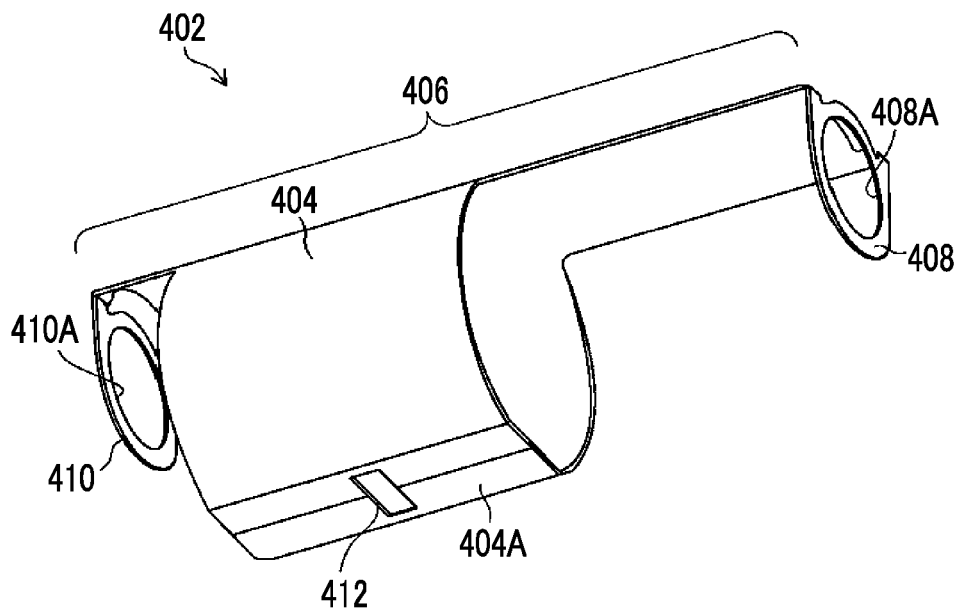
FIG. 10 is a perspective view illustrating only a coupling ring.

Only the coupling ring 402 is illustrated in FIG. 10. The coupling ring 402 has a tubular ring part 404 that surrounds an outer periphery of the partition wall member 324 in the circumferential direction and that comes into contact with contacts or approaches an outer peripheral surface of the partition wall member 324 in portions other than endoscope guide groove 326 and treatment tool guide groove 328, and an arm part 406 consisting of a portion that faces the treatment tool guide groove 328 of the ring part 404 and a portion that extends in the forward-backward direction from the ring part 404 along a position that faces the treatment tool guide groove 328.

The arm part 406 acts as a second engaging part that is engaged with the treatment tool fixing tool 450 (refer to FIG. 6) that is the second fixing tool, and a proximal end and a distal end of the arm part are respectively provided with a rear restriction end 408 and a front restriction end 410 that are a second restricting part which restricts the forward and backward movement of the treatment tool fixing tool 450 and that are inserted into and disposed in the inside of the treatment tool guide groove 328. Also, the rear restriction end 408 and the front restriction end 410 are respectively provided with openings 408A and 410A through which the treatment tool insertion part 202 is inserted.

Additionally, a first engaging part 404A, which is engaged with the endoscope fixing tool 430 that is the first fixing tool and which extends in a leftward-rightward direction along a plane orthogonal to the forward-backward direction, is formed in a portion that is disposed to face the endoscope guide groove 326 in the ring part 404.

The rotation of the coupling ring 402 in the direction around the axis (a direction around the reference axis 300a) with respect to the partition wall member 324 is restricted by the rear restriction end 408 and the front restriction end 410 that are inserted into and disposed inside the first engaging part 404A and the treatment tool guide groove 328.

Also, the coupling ring 402 is supported so as to be movable forward and backward in the forward-backward direction by the partition wall member 324 within the long tubular overtube part 320, and is supported in a state where the movement of the slider in the upward-downward direction and in the leftward-rightward direction and the rotation of the slider in all directions (direction around three axes including a forward-backward axis, a leftward-rightward axis, and an upward-downward direction) are restricted (a state where the rotation of the slider around at least the reference axis 300a is impossible). Additionally, the coupling ring 402 moves forward and backward within a movable range having a position where the coupling ring 402 (rear restriction end 408) abuts against the proximal end cap 340 as a rear end, and having a position where the coupling ring 402 (front restriction end 410) abuts against the distal end cap 360 as a front end.

Figure 11:
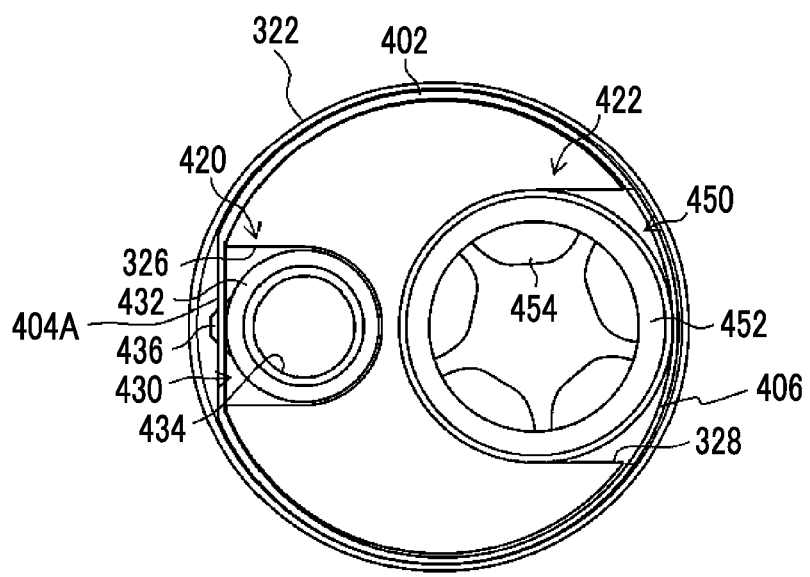
FIG. 11 is a cross-sectional view when viewed from arrow A-A in FIG. 6.
Figure 12:
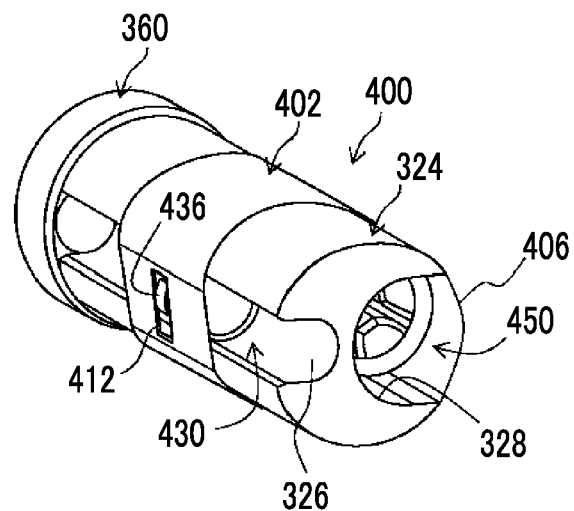
FIG. 12 is a perspective view illustrating a portion of the overtube in the state of FIG. 7.
Figure 13:
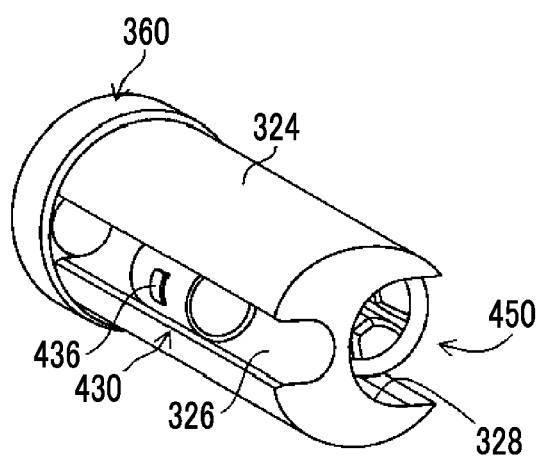
FIG. 13 is a perspective view illustrating the overtube of FIG. 12 with the coupling ring omitted.
Figure 14:
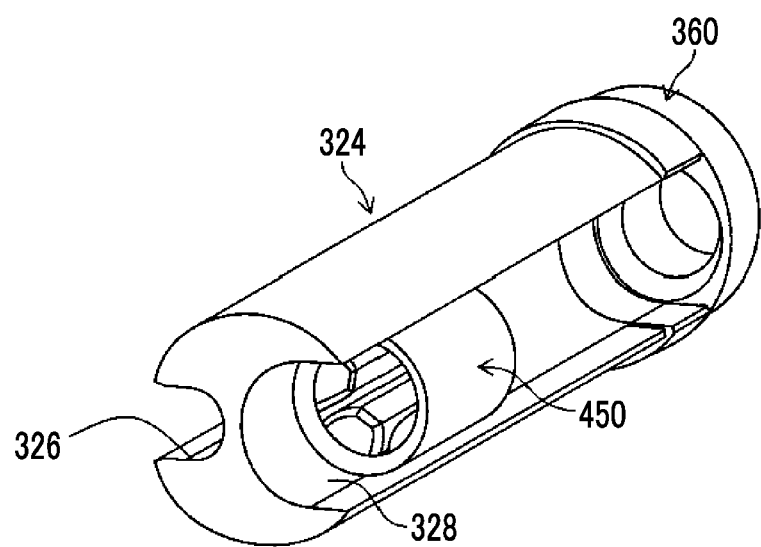
FIG. 14 is a perspective view illustrating the overtube of FIG. 13 from a right side.

FIG. 11 is a cross-sectional view when viewed from arrow A-A in FIG. 6, and FIG. 12 is a perspective view illustrating the overtube 300 cut by in a plane perpendicular to the reference axis 300a at a position that intersects the arm part 406 closer to the proximal end side than the ring part 404 of the coupling ring 402 in the state of FIG. 7. FIG. 13 is a perspective view illustrating the overtube of FIG. 12 with the coupling ring 402 omitted, and FIG. 14 is a perspective view illustrating the overtube 300 of FIG. 13 from a right side.

As illustrated in FIGS. 6 and 11, the slider 400 has a left endoscope coupling part 420 that is coupled to (engaged with) the endoscope insertion part 102 inside the coupling ring 402 and a right treatment tool coupling part 422 that is coupled to (engaged with) the treatment tool insertion part 202.

That is, the slider 400 has an endoscope coupling part 420 as the first coupling part coupled to the first insertion part of the first medical instrument inserted through the first insertion passage, and a treatment tool coupling part 422 as the second coupling part coupled to the second insertion part of the second medical instrument inserted through the second insertion passage.

Specifically, as illustrated in FIGS. 6, 11, and 13, the endoscope coupling part 420 provided on a left side of the slider 400 includes the endoscope fixing tool 430 that is disposed inside the endoscope guide groove 326 and that is one form of the first fixing tool that is movable forward and backward in the forward-backward direction along the endoscope insertion passage 306.

The endoscope fixing tool 430 is constituted by a tubular frame 432 that approaches or comes into contact with an inner wall surface of the endoscope guide groove 326, and a tubular pressure-contact member 434 that is fixed inside the frame 432 and formed of an elastic material, such as elastic rubber.

An outer peripheral part of the frame 432 is provided with a protrusion 436 that protrudes in the radial direction from a position in the circumferential direction at a position that faces an opening of the endoscope guide groove 326. As illustrated in FIGS. 6, 10, and 12, the protrusion 436 is inserted through an engagement hole 412 that is one form of a first restricting part formed in the first engaging part 404A in the ring part 404 of the coupling ring 402, and is locked to the engagement hole 412 in the forward-backward direction.

According to this, due to the engagement between the protrusion 436 of the endoscope fixing tool 430 and the engagement hole 412 of the coupling ring 402, the endoscope fixing tool 430 and the first engaging part 404A are engaged with each other and the relative forward and backward movement of the endoscope fixing tool 430 in the forward-backward direction with respect to the coupling ring 402 is restricted. Hence, the coupling ring 402 and the endoscope fixing tool 430 integrally move forward and backward in the forward-backward direction.

Additionally, when the endoscope insertion part 102 has been inserted through the endoscope insertion passage 306, the endoscope insertion part 102 is inserted through the inside of the pressure-contact member 434, and the endoscope fixing tool 430 is fixed to the endoscope insertion part 102 by the pressure-contact member 434 being brought into pressure contact with (engaged with) the outer peripheral surface of the endoscope insertion part 102. Then, the central axis of the endoscope insertion part 102 is disposed substantially coaxially with the endoscope insertion axis 306a.

Accordingly, the endoscope insertion part 102 and the slider 400 (coupling ring 402) are coupled to (engaged with) each other in an interlocking manner via the endoscope fixing tool 430, and the slider 400 (coupling ring 402) also integrally moves forward and backward in an interlocking manner with the forward and backward movement of the endoscope insertion part 102 in the forward-backward direction (axial direction).

In addition, since the coupling herein is based on the elastic force of the pressure-contact member 434, the engagement position (the position of the endoscope insertion part 102 where the slider 400 is engaged) of the endoscope insertion part 102 coupled to the slider 400 (coupling ring 402) can be arbitrarily adjusted.

Additionally, the frame 432 of the endoscope fixing tool 430 has a shape such that the movement (rotation) thereof is impossible in the direction around the axis inside the endoscope guide groove 326, and the endoscope fixing tool 430 is allowed only to move forward and backward in the forward-backward direction within the endoscope guide groove 326.

Specifically, as illustrated in FIGS. 6, 11, and 14, the treatment tool coupling part 422 provided on a right side of the slider 400 includes the treatment tool fixing tool 450 that is disposed in a range between the rear restriction end 408 and the front restriction end 410 (refer to FIG. 10 or the like) of the arm part 406 of the coupling ring 402 inside the treatment tool guide groove 328, and that is the second fixing tool that is movable forward and backward along the treatment tool guide groove 328.

The treatment tool fixing tool 450 is constituted by a tubular frame 452 that approaches or comes into contact with an inner wall surface of the treatment tool guide groove 328, and a tubular pressure-contact member 454 that is fixed inside the frame 452 and formed of an elastic material, such as elastic rubber. In addition, an inner peripheral surface of the pressure-contact member 454 is formed in a shape such that regularities are repeated in the circumferential direction so as to be appropriately engageable with treatment tool insertion parts 202 having a plurality of types of greatly different diameters.

According to this, when the treatment tool insertion part 202 has been inserted through the treatment tool insertion passage 308, the treatment tool insertion part 202 is inserted through the inside of the pressure-contact member 454, and the treatment tool fixing tool 450 is fixed to the treatment tool insertion part 202 by the pressure-contact member 454 being brought into pressure contact with (engaged with) the outer peripheral surface of the treatment tool insertion part 202. Then, the central axis of the treatment tool insertion part 202 is disposed substantially coaxially with the treatment tool insertion axis 308a.

Accordingly, the treatment tool fixing tool 450 also integrally moves forward and backward in an interlocking manner with the forward and backward movement of the treatment tool insertion part 202 in the forward-backward direction (axial direction). Additionally, the treatment tool fixing tool 450 also rotates inside the treatment tool guide groove 328 in an interlocking manner with the rotation of the treatment tool insertion part 202 around the axis thereof.

In addition, since the coupling between the treatment tool insertion part 202 and the treatment tool fixing tool 450 herein is based on the elastic force of the pressure-contact member 454, the engagement position (the position of the treatment tool insertion part 202 where the treatment tool fixing tool 450 is engaged) of the treatment tool insertion part 202 coupled to the treatment tool fixing tool 450 can be arbitrarily adjusted.

Additionally, the rear restriction end 408 in the arm part 406 of the coupling ring 402 is disposed on a rear side of the treatment tool fixing tool 450, and the front restriction end 410 in the arm part 406 is disposed on a front side of the treatment tool fixing tool 450.

Hence, the arm part 406 allows the forward and backward movement of the treatment tool fixing tool 450 in the forward-backward direction with respect to the coupling ring 402 in a range from a position where the treatment tool fixing tool 450 abuts against the rear restriction end 408 to a position where the treatment tool fixing tool 450 abuts against the front restriction end 410, and restricts the treatment tool fixing tool 450 in that range.

In addition, in a case where a range where the treatment tool fixing tool 450 is movable forward and backward with respect to the coupling ring 402 is defined as a second range and a range where the of the endoscope fixing tool 430 is movable forward and backward with respect to the coupling ring 402 is defined as a first range, the first range becomes zero because the forward and backward movement of the endoscope fixing tool 430 in the forward-backward direction with respect to the first engaging part 404A of the coupling ring 402 is restricted as described above.

Accordingly, the coupling ring 402 has a non-sensing region where either the endoscope fixing tool 430 or the treatment tool fixing tool 450 is not moved forward and backward with the forward and backward movement of the other of the endoscope fixing tool 430 and the treatment tool fixing tool 450.

Meanwhile, in a case where the treatment tool fixing tool 450 moves forward and backward in the forward-backward direction or in a case where the coupling ring 402 moves forward and backward in the forward-backward direction together with the endoscope fixing tool 430, the treatment tool fixing tool 450 abuts against the rear restriction end 408 or the front restriction end 410. In this state, the coupling ring 402 has a sensing region where either the endoscope fixing tool 430 or the treatment tool fixing tool 450 is moved forward and backward movement with respect to the forward and backward movement (the forward and backward movement in a direction in which the treatment tool fixing tool 450 and the rear restriction end 408 or the front restriction end 410 are not spaced apart from each other) of other of the endoscope fixing tool 430 and the treatment tool fixing tool 450.

Due to the configuration of the above slider 400, the slider 400 has the non-sensing region where either the endoscope insertion part 102 inserted through the endoscope insertion passage 306 of the overtube 300 and coupled to the endoscope fixing tool 430 or the treatment tool insertion part 202 inserted through the treatment tool insertion passage 308 and coupled to the treatment tool fixing tool 450 does not move forward and backward without interlocking with the forward and backward movement of the other in the forward-backward direction (axial direction) and the sensing region where either the endoscope insertion part 102 or the treatment tool insertion part 202 moves forward and backward in an interlocking manner with the forward and backward movement of the other. That is, the endoscope insertion part 102 is adapted to interlock with the forward and backward movement of the treatment tool insertion part 202 in the axial direction with play by the slider 400.

In addition, although the first range where the endoscope fixing tool 430 is movable forward and backward with respect to the coupling ring 402 is zero in the present embodiment, the forward and backward movement of the endoscope fixing tool 430 together with the treatment tool fixing tool 450 with respect to the coupling ring 402 or instead of the treatment tool fixing tool 450 may be allowed, and the first range may have a magnitude other than zero. Namely, a configuration in which the forward and backward movement of at least one of the endoscope fixing tool 430 and the treatment tool fixing tool 450 with respect to the coupling ring 402 is allowed may be adopted.

In a case where the forward and backward movement of the endoscope fixing tool 430 with respect to the coupling ring 402 is allowed, for example, it is possible to adopt a form in which the range of the engagement hole 412 (refer to FIGS. 6 and 10, or the like) formed in the first engaging part 404A of the coupling ring 402 and engaged with the protrusion 436 of the endoscope fixing tool 430 is increased in the forward-backward direction. Accordingly, the endoscope fixing tool 430 can be made movable forward and backward with respect to the coupling ring 402 with the length range of the engagement hole 412 in the forward-backward direction as the first range. Otherwise, by virtue of the same configuration as the rear restriction end 408 and the front restriction end 410 of the arm part 406 with respect to the treatment tool fixing tool 450, the endoscope fixing tool 430 can be made movable forward and backward with respect to the coupling ring 402.

Additionally, in the present embodiment, the treatment tool fixing tool 450 may be made rotatable around an axis (treatment tool insertion axis 308a) within the treatment tool insertion passage 308, and the treatment tool insertion part 202 may be made easily rotatable around the axis, the rotation of the treatment tool fixing tool 450 around the axis may be restricted. In this case, the above configuration in the case where the forward and backward movement of the endoscope fixing tool 430 with respect to the coupling ring 402 is allowed can also be adopted for the treatment tool fixing tool 450. In addition, the endoscope fixing tool 430 may be rotatable around an axis (endoscope insertion axis 306a) within the endoscope insertion passage 306. In that case, the configuration of the second engaging part (arm part 406) of the coupling ring 402 with respect to the treatment tool fixing tool 450 can be adopted for the endoscope fixing tool 430.

The working of the overtube 300 configured as described above will be described together with the operation in a case where the treatment of a diseased site within a patient's body cavity is performed using the endoscopic surgical device 10.

Figure 15:
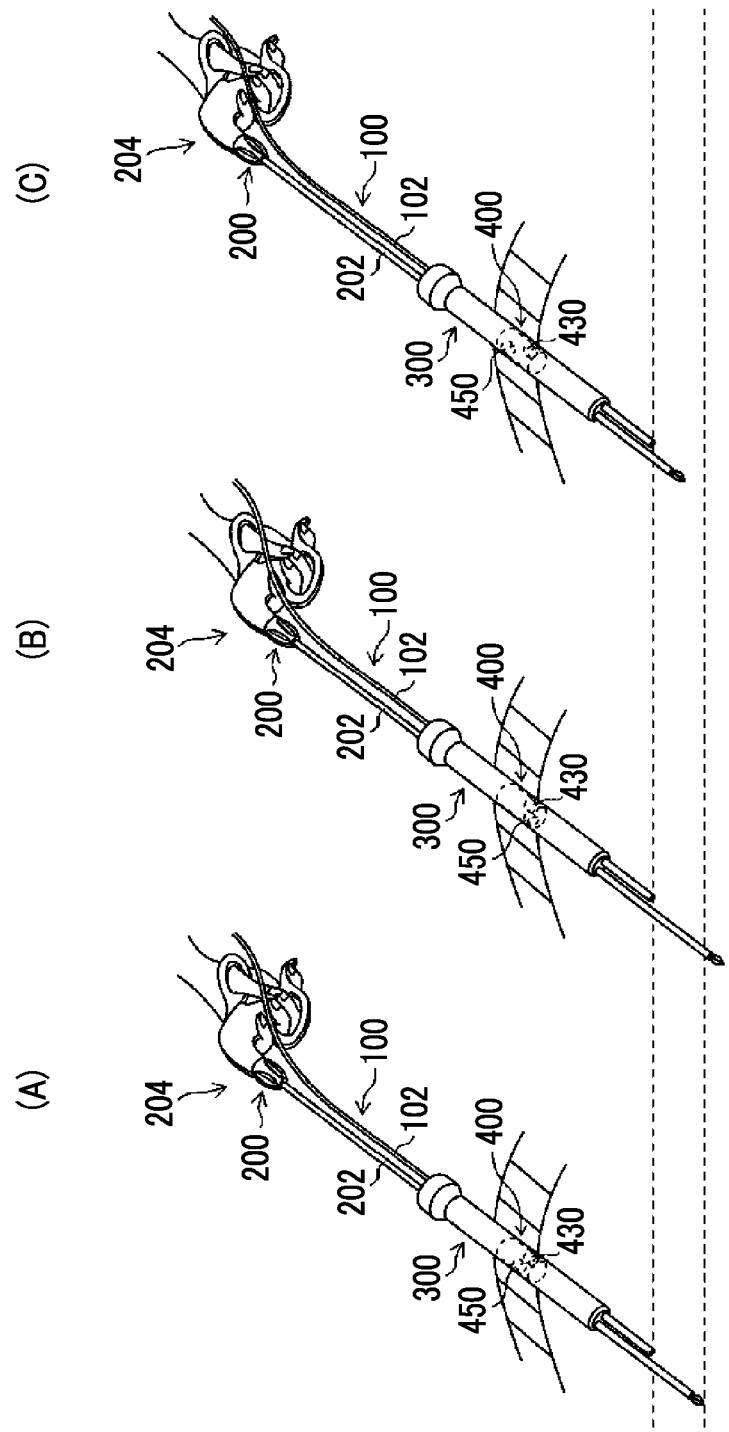
FIG. 15 is an explanatory view illustrating a state of the operation in a case where the diseased site within the patient's body cavity is treated using the endoscopic surgical device.

First, as illustrated in portion (A) of FIG. 15, after the overtube 300 is inserted into a patient's body wall and a pneumoperitoneum gas is injected into a body cavity, the endoscope 100 (endoscope insertion part 102) and the treatment tool 200 (treatment tool insertion part 202) are respectively inserted into the endoscope insertion passage 306 and the treatment tool insertion passage 308 of the overtube 300, and the endoscope insertion part 102 and the treatment tool insertion part 202 are mounted on the overtube 300.

In this case, the endoscope insertion part 102 is reliably guided to a position, where the endoscope fixing tool 430 of the slider 400 is inserted, by the endoscope guide groove 326 of the partition wall member 324, and is coupled to the endoscope fixing tool 430.

Similarly, the treatment tool insertion part 202 is guided reliably to a position, where the treatment tool fixing tool 450 of the slider 400 is inserted, by the treatment tool guide groove 328 of the partition wall member 324, and is coupled to the treatment tool fixing tool 450.

Figure 16:
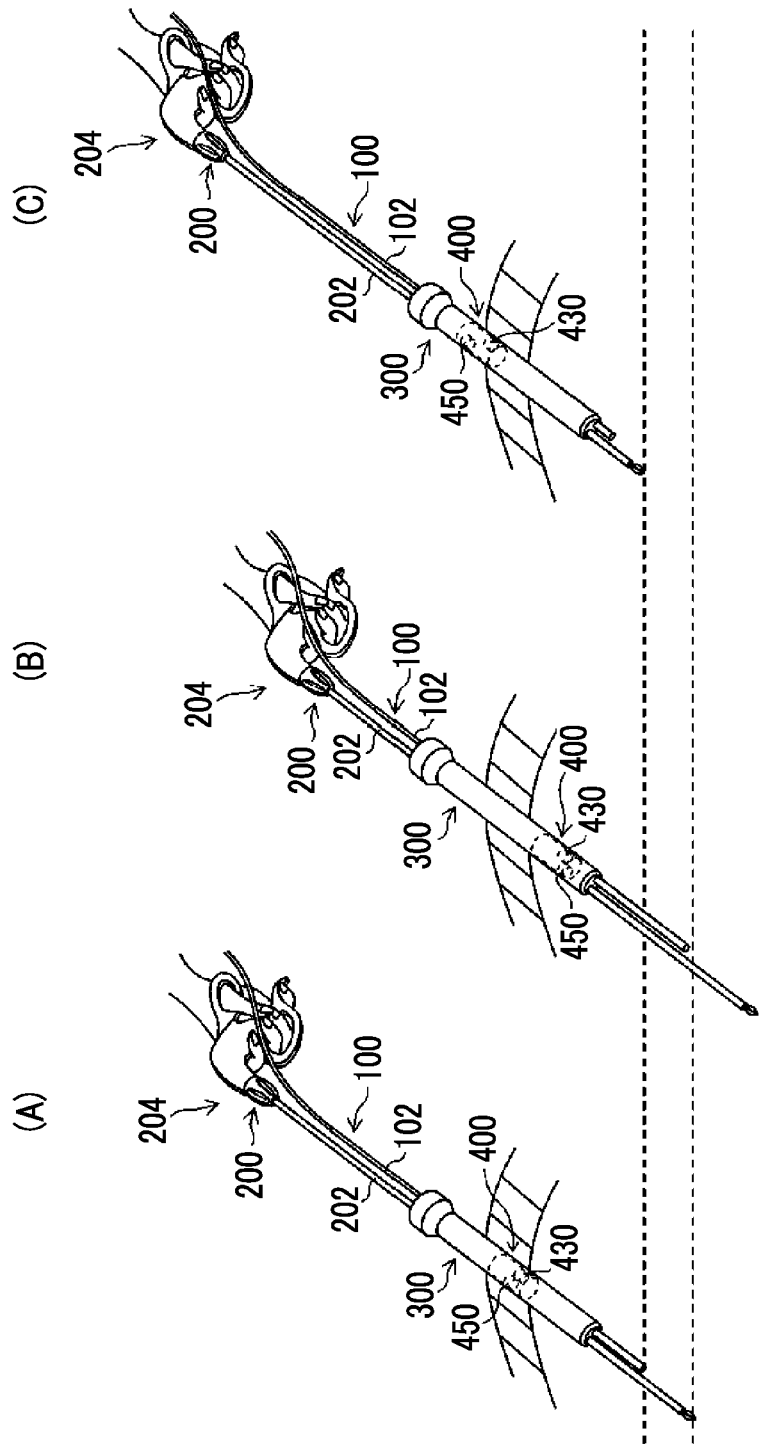
FIG. 16 is an explanatory view illustrating a state of the operation in a case where the diseased site within the patient's body cavity is treated using the endoscopic surgical device.

In addition, although the sheathing tube 500 is not illustrated in FIG. 15, and FIG. 16 illustrated therebelow, the sheathing tube 500 is fitted to the overtube 300 as illustrated in FIG. 3. However, it is also possible to use the overtube 300 without fitting the sheathing tube 500 thereto.

Figure 17:
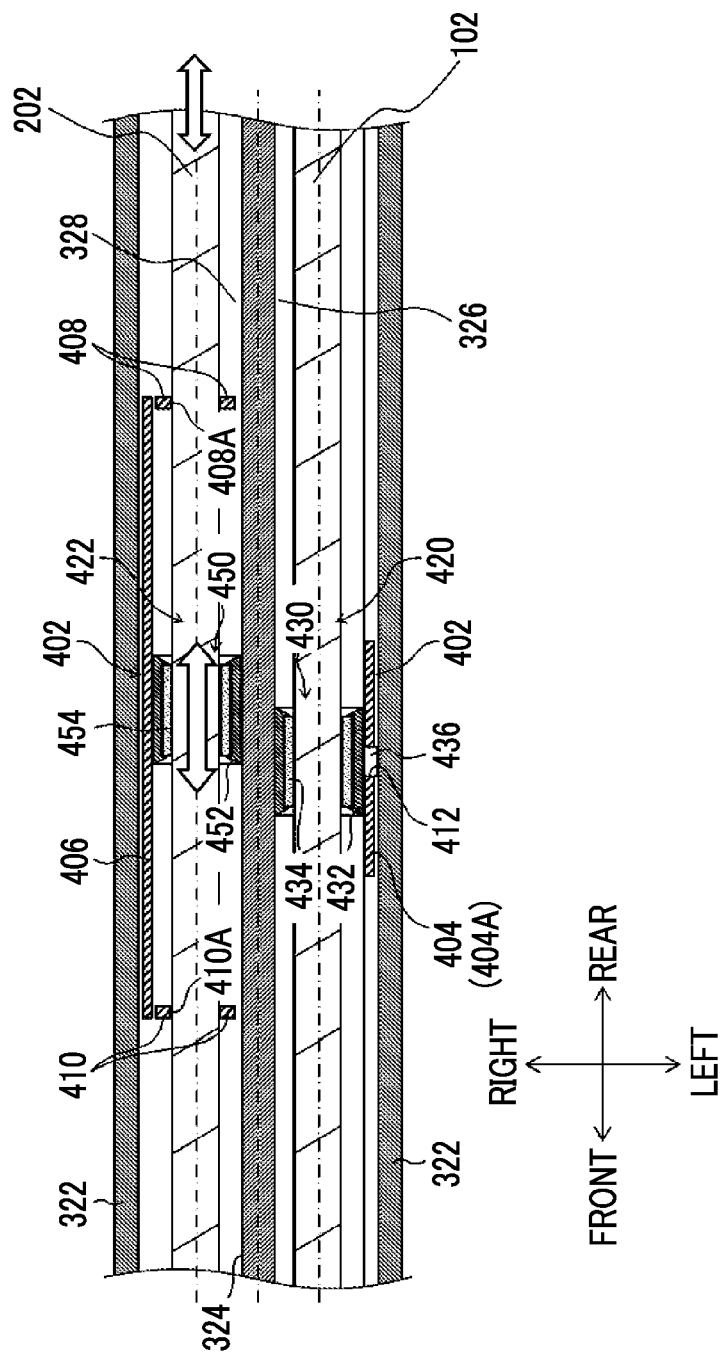
FIG. 17 is a cross-sectional view illustrating one state of a slider.

It is assumed that the state of portion (A) of FIG. 15 is a state illustrated in FIG. 17. FIG. 17 is a cross-sectional view illustrating the state of the slider 400 coupled to the endoscope insertion part 102 and the treatment tool insertion part 202, and illustrating a state where the treatment tool fixing tool 450 reaches neither a front end nor a rear end of a movable range thereof with respect to the coupling ring 402 (arm part 406). That is, a state where the treatment tool fixing tool 450 reaches neither the rear restriction end 408 nor the front restriction end 410 is illustrated.

In this case, if the operator minutely moves the treatment tool insertion part 202 forward with his/her hand that is gripping the operating part 204 of the treatment tool 200, only the treatment tool fixing tool 450 moves forward within the movable range thereof with respect to the coupling ring 402, and the coupling ring 402 does not move with respect to the overtube 300 (long tubular overtube part 320).

For that reason, with respect to the forward movement of the treatment tool insertion part 202 until the treatment tool fixing tool 450 reaches the front end (front restriction end 410) of the movable range thereof with respect to the coupling ring 402, as illustrated in portion (B) FIG. 15, only the treatment tool insertion part 202 moves forward in a state where the endoscope insertion part 102 is stationary. That is, the slider 400 has the non-sensing region where the endoscope insertion part 102 does not interlock with the forward and backward movement of the treatment tool insertion part 202, and the forward movement operation of the treatment tool 200 at this time becomes a forward and backward movement operation of the slider 400 in the non-sensing region.

Similarly, in the state illustrated in FIG. 17, if the operator minutely moves the treatment tool insertion part 202 backward with his/her hand that is gripping the operating part 204 of the treatment tool 200, only the treatment tool fixing tool 450 moves backward within the movable range thereof with respect to the coupling ring 402, and the coupling ring 402 does not move with respect to the overtube 300 (long tubular overtube part 320).

For that reason, with respect to the backward movement of the treatment tool insertion part 202 until the treatment tool fixing tool 450 reaches the rear end (rear restriction end 408) of the movable range thereof with respect to the coupling ring 402, as illustrated in portion (C) of FIG. 15(C), only the treatment tool insertion part 202 moves backward in a state where the endoscope insertion part 102 is stationary. That is, the backward movement operation of the treatment tool 200 at this time becomes a backward movement operation of the slider 400 in the non-sensing region.

Hence, since the endoscope 100 does not move forward and backward with respect to the minute forward and backward movement operation of the treatment tool 200, that is, the forward and backward movement operation thereof in the non-sensing region, the range of an observation site, such as a distal end site of the treatment tool 200 or a body cavity inner site, to be displayed on the monitor 112 as an endoscopic image does not vary, and the size of an image of the observation site can be prevented from fluctuating according to minute displacement of the treatment tool 200. Accordingly, a sense of perspective can be suitably maintained, and a stable endoscopic image can be provided.

Figure 18:
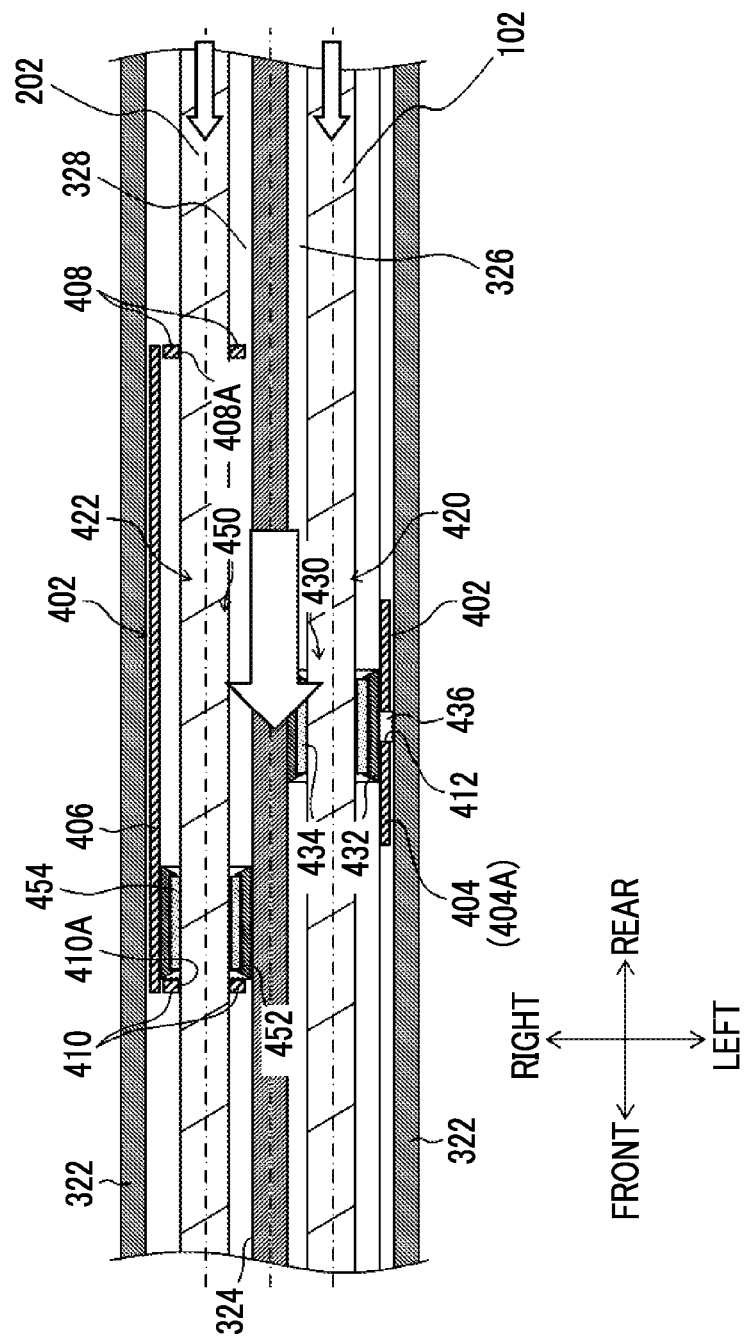
FIG. 18 is a cross-sectional view illustrating one state of the slider.

Meanwhile, if the operator greatly moves the treatment tool insertion part 202 forward with his/her hand that is gripping the operating part 204 of the treatment tool 200 in the state illustrated in FIG. 17, a state where the treatment tool fixing tool 450 reaches the front end (front restriction end 410) of the movable range thereof with respect to the coupling ring 402 as illustrated in FIG. 18 is brought out after the forward movement of the treatment tool fixing tool 450 of the slider 400 in the non-sensing region until it abuts against the front end (front restriction end 410) of the movable range. Then, in a case where the treatment tool insertion part 202 further moves forward, the treatment tool fixing tool 450 and the coupling ring 402 move forward with respect to the long tubular overtube part 320 together with the treatment tool insertion part 202. Then, the endoscope fixing tool 430 moves forward together with the coupling ring 402, and the endoscope insertion part 102 moves forward together with the endoscope fixing tool 430. Accordingly, the endoscope insertion part 102 moves forward in an interlocking manner with the treatment tool insertion part 202.

For that reason, with respect to the forward movement of the treatment tool insertion part 202 after the treatment tool fixing tool 450 reaches the front end (front restriction end 410) of the movable range thereof with respect to the coupling ring 402, the endoscope insertion part 102 moves forward in an interlocking manner with the treatment tool insertion part 202 as illustrated in portion (B) of FIG. 16, compared to the state of portion (A) of FIG. 16 illustrating the same state as portion (A) of FIG. 15. That is, the slider 400 has the sensing region where the endoscope insertion part 102 interlocks with the forward and backward movement of the treatment tool insertion part 202, and the forward movement operation of the treatment tool 200 at this time becomes a forward movement operation of the slider 400 in the sensing region.

Figure 19:
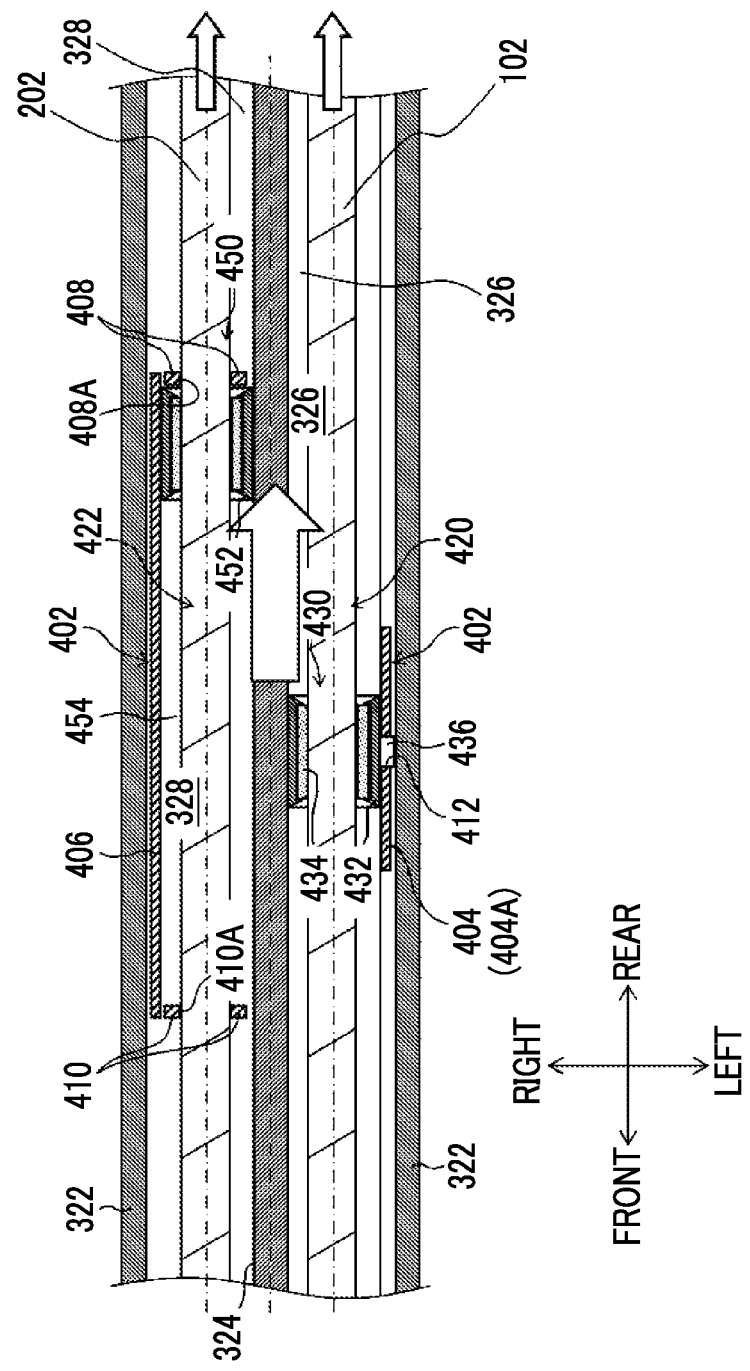
FIG. 19 is a cross-sectional view illustrating one state of the slider.

Similarly, if the operator greatly moves the treatment tool insertion part 202 backward with his/her hand that is gripping the operating part 204 of the treatment tool 200 in the state illustrated in FIG. 17, a state where the treatment tool fixing tool 450 reaches the rear end (rear restriction end 408) of the movable range thereof with respect to the coupling ring 402 as illustrated in FIG. 19 is brought out after the backward movement of the treatment tool fixing tool 450 of the slider 400 in the non-sensing region until it abuts against the rear end (rear restriction end 408) of the movable range. Then, in a case where the treatment tool insertion part 202 further moves backward, the treatment tool fixing tool 450 and the coupling ring 402 moves backward with respect to the long tubular overtube part 320 together with the treatment tool insertion part 202. Then, the endoscope fixing tool 430 moves backward together with the coupling ring 402, and the endoscope insertion part 102 moves backward together with the endoscope fixing tool 430. Accordingly, the endoscope insertion part 102 moves backward in an interlocking manner with the treatment tool insertion part 202.

For that reason, with respect to the backward movement of the treatment tool insertion part 202 after the treatment tool fixing tool 450 reaches the rear end (rear restriction end 408) of the movable range thereof with respect to the coupling ring 402, as illustrated in portion (C) of FIG. 16, the endoscope insertion part 102 moves backward in an interlocking manner with the treatment tool insertion part 202. That is, the backward movement operation of the treatment tool 200 at this time becomes a backward movement operation of the slider 400 in the sensing region.

Hence, since the endoscope 100 moves forward and backward with respect to a large forward and backward movement operation of the treatment tool 200, that is, the forward and backward movement operation thereof in the sensing region, the range of an observation site that appears in an endoscopic image to be displayed on the monitor 112 is continuously changed so as to follow the forward and backward movement of the treatment tool 200. Since the size of images of observation sites other than the distal end site of the treatment tool 200 that appears in the endoscopic image according to the operation of the treatment tool 200, and the size of the range of the observation site varies, the operator can simply obtain a desired image.

As described above, in a case where the displacement of the treatment tool insertion part 202 in the axial direction is large (in a case where a large amplitude of forward and backward movement operation has been performed) when an operator has moved the treatment tool insertion part 202 forward and backward in the axial direction, the endoscope insertion part 102 also moves forward, backward, up, down, right, and left in an interlocking manner. Thus, the visual field, orientation, and the like of the endoscope 100 can be changed as intended by an operator. Additionally, the visual field is always given to pick up an image of the distal end site of the treatment tool 200 and consequently, an image that is optimal for treatment is automatically provided. In a case where it is desired to check sites other than a site to be treated, the checking can be performed by moving the treatment tool insertion part 202, and an operator can perform operations as desired. Hence, an assistant (endoscopic technician) who operates the endoscope 100 apart from the operator can be made unnecessary, and a troublesome condition in which the operator should instruct an assistant about the visual field, orientation, and the like of the endoscope 100 serially can be eliminated.

Additionally, in a case where the displacement of the treatment tool insertion part 202 in the axial direction is small (in a case where a small amplitude of forward and backward movement has been performed), the endoscope insertion part 102 does not interlock. Therefore, an endoscopic image can be prevented from fluctuating unnecessarily, a sense of perspective can be suitably maintained, and a stable endoscopic image can be provided.

As described above, in the above embodiment, the slider 400 (coupling ring 402) had the non-sensing region where either the endoscope insertion part 102 (endoscope fixing tool 430) or the treatment tool insertion part 202 (treatment tool fixing tool 450) does not move forward and backward with respect to the forward and backward movement of the other. However, the invention can also be applied to a case where the slider 400 (coupling ring 402) has no such a non-sensing region and has only the sensing region where either the endoscope insertion part 102 (endoscope fixing tool 430) or the treatment tool insertion part 202 (treatment tool fixing tool 450) moves forward and backward with respect to the forward and backward movement of the other.

Additionally, in the above embodiment, the endoscope insertion passage 306 that is one form of the first insertion passage of the overtube 300 may be used as the second insertion passage, and the treatment tool insertion passage 308 that is one form of the second insertion passage may be used as the first insertion passage.

Additionally, in the overtube 300 of the above embodiment, the insertion passage through which the endoscope 100 (endoscope insertion part 102) is inserted is used as the first insertion passage, and the insertion passage through which the treatment tool 200 (treatment tool insertion part 202) is inserted is used as the second insertion passage. The invention is not limited to this, and can be applied to an overtube including the first insertion passage through which the first insertion part of the first medical instrument of the first medical instrument and the second medical instrument that are arbitrary types of two medical instruments is inserted, and the second insertion passage through which the second insertion part of the second medical instrument is inserted.

Additionally, in the overtube 300 of the above embodiment, the endoscope insertion passage 306 that is the first insertion passage, and the treatment tool insertion passage 308 that is the second insertion passage are disposed parallel to each other. However, the invention is not limited to this, and can also be applied to overtubes in which the first insertion passage and the second insertion passage obliquely intersect each other.

That is, in the above embodiment, if the endoscope insertion axis 306a that is the central axis of the endoscope insertion passage 306 and the treatment tool insertion axis 308a that is the central axis of the treatment tool insertion passage 308 are parallel to the reference axis 300a, and the endoscope insertion axis 306a and the treatment tool insertion axis 308a are parallel to each other, these axes may not be necessarily parallel to each other.

For example, the invention can also be applied to a form in which the treatment tool insertion passage 308 that is the second insertion passage is disposed parallel to the reference axis 300a as in the above embodiment, and the endoscope insertion passage 306 that is the first insertion passage is disposed to obliquely intersect the reference axis 300a. The overtube of this form will be specifically described as a modification example of the overtube 300 of the above embodiment. In the following embodiment shown as the modification example, constituent elements having functions that are the same as or similar to those of the constituent elements of the above embodiment will be designated by the same reference signs.

Figure 20:
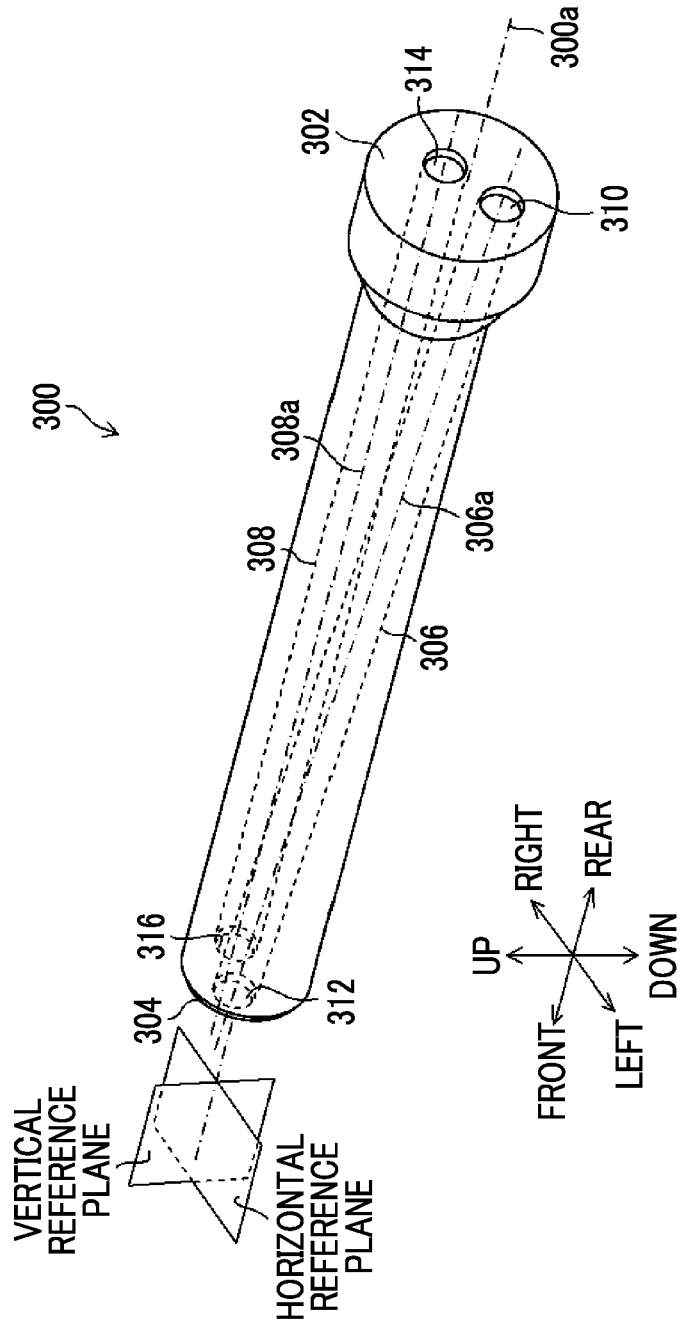
FIG. 20 is an external perspective view in another embodiment of the overtube.

FIG. 20 is an external perspective view of the overtube 300 that is the modification example.

In this drawing, the treatment tool insertion axis 308a of the treatment tool insertion passage 308 is disposed parallel to the reference axis 300a of the overtube 300, and the endoscope insertion axis 306a of the endoscope insertion passage 306 obliquely intersects the reference axis 300a.

That is, in a case where a plane along the upward-downward direction including the reference axis 300a is referred to as a vertical reference plane and a plane along the leftward-rightward direction including the reference axis 300a is referred to as a horizontal reference plane, the treatment tool insertion axis 308a is parallel to both the horizontal reference plane and the vertical reference plane.

Meanwhile, the endoscope insertion axis 306a is parallel to the vertical reference plane and is not parallel to the horizontal reference plane. That is, the endoscope insertion axis 306a is obliquely inclined with respect to the horizontal reference plane. Also, the endoscope insertion axis 306a is inclined from a rear lower side toward a front upper side, and for example, intersects the horizontal reference plane at a substantially intermediate position of the overtube 300 in the forward-backward direction.

In a case where the overtube 300 illustrated in this FIG. 20 is configured, the endoscope guide groove 326 in the long tubular overtube part 320, the through-hole 342 in the proximal end cap 340, and the through-hole 362 in the distal end cap 360 are obliquely formed with respect to the horizontal reference plane along the endoscope insertion axis 306a.

Figure 21:
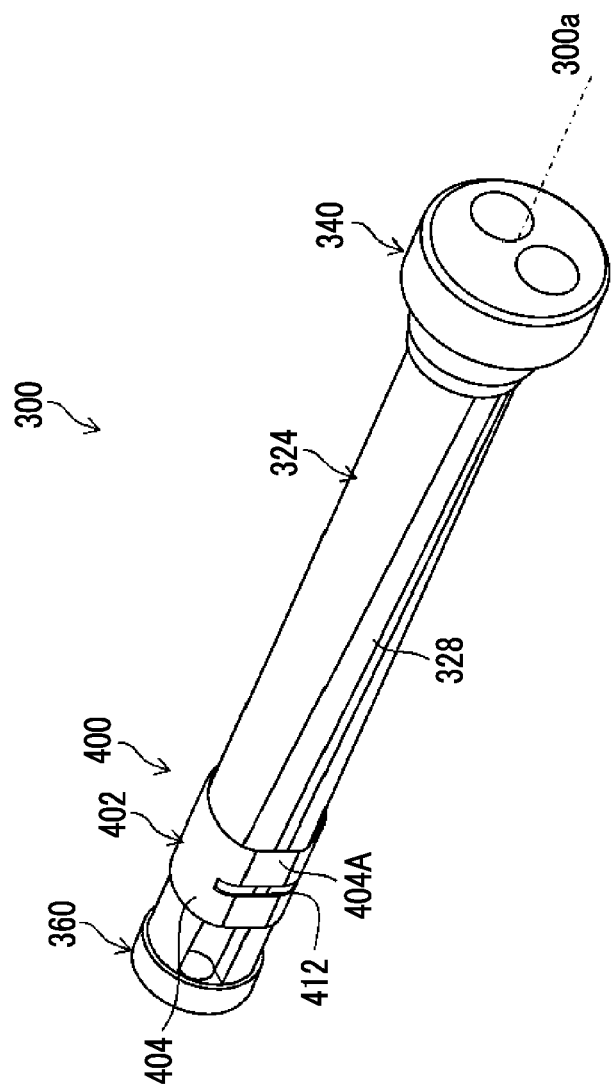
FIG. 21 is a perspective view illustrating the overtube of FIG. 20 with the long tubular body of the long tubular overtube part omitted.
Figure 22:
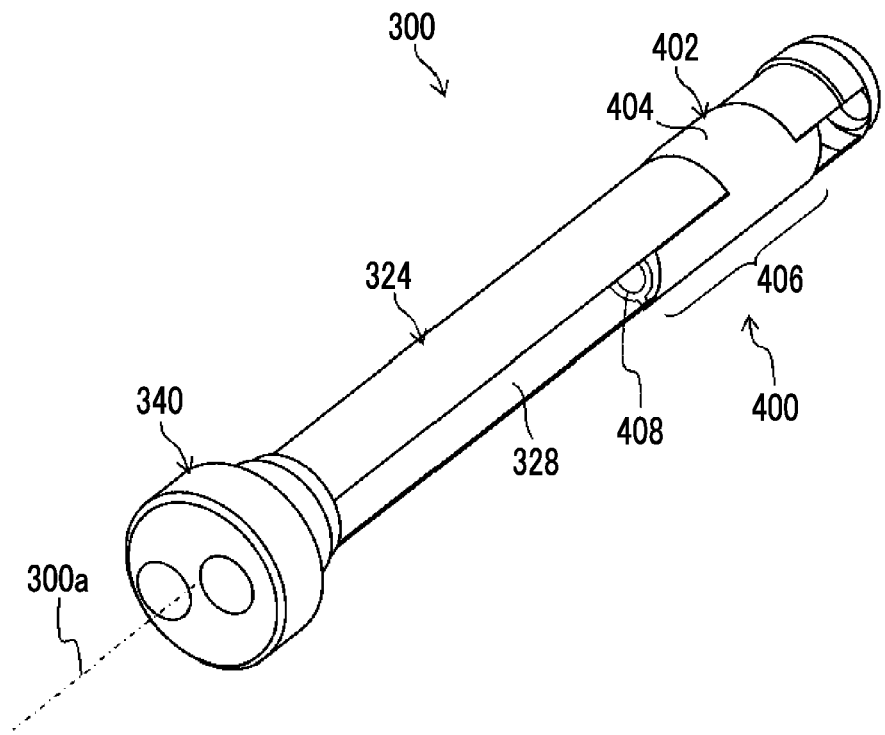
FIG. 22 is a perspective view illustrating the overtube of FIG. 20 with the long tubular body of the long tubular overtube part omitted.

FIGS. 21 and 22 are perspective views illustrating the partition wall member 324 and the slider 400 in the long tubular overtube part 320 in a case where the overtube 300 of FIG. 20 is configured. As illustrated in FIG. 22, the treatment tool guide groove 328 of the partition wall member 324 is formed along the treatment tool insertion axis 308a parallel to the reference axis 300a as in the above embodiment.

Meanwhile, as illustrated in FIG. 21, the endoscope guide groove 326 of the partition wall member 324 is not parallel to the reference axis 300a, and is formed along the endoscope insertion axis 306a that is oblique with respect to the horizontal reference plane.

Additionally, since the endoscope fixing tool 430 disposed inside the endoscope guide groove 326 moves also in the upward-downward direction with respect to the partition wall member 324 and the coupling ring 402 together with the forward and backward movement in the forward-backward direction, the protrusion 436 formed on the outer peripheral part of the endoscope fixing tool 430 also moves in the upward-downward direction with respect to the coupling ring 402 according to the position of the endoscope fixing tool 430 in the forward-backward direction.

Figure 23:
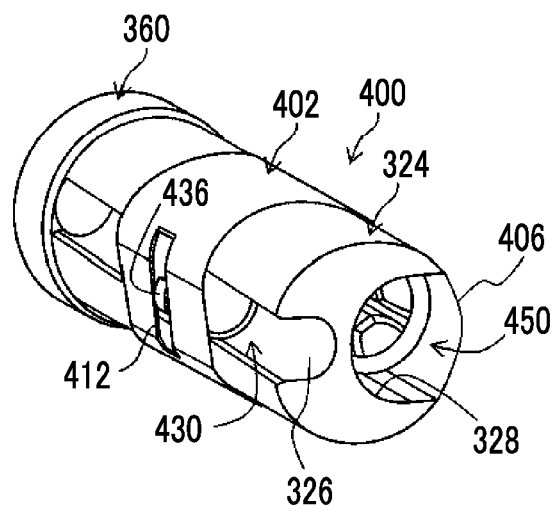
FIG. 23 is a perspective view illustrating a portion of the overtube of FIG. 20.

Thus, the engagement hole 412 formed in the flat first engaging part 404A of the coupling ring 402 is formed as an elongated hole that extends in the circumferential direction (upward-downward direction) beyond the range of the first engaging part 404A as illustrated in the enlarged view of FIG. 23 so as to be engaged with of the protrusion 436 at an arbitrary position of a movement range of the protrusion 436 in the upward-downward direction.

Additionally, since the first engaging part 404A of the coupling ring 402 is the plane orthogonal to the leftward-rightward direction, the distance between the outer peripheral surface of the endoscope fixing tool 430 (not illustrated) and the first engaging part 404A is uniformly maintained irrespective of the movement of the endoscope fixing tool 430 in the upward-downward direction with respect to the coupling ring 402. For that reason, the amount of protrusion of the protrusion 436 can be reduced, and the diameter of the long tubular overtube part 320 can be reduced.

Meanwhile, in a case where the endoscope guide groove 326 is obliquely formed, the opening of the endoscope guide groove 326 deviates from a position that faces the first engaging part 404A. Therefore, the range of the partition wall member 324 through which the first engaging part 404A passes due to the movement of the coupling ring 402 in the forward-backward direction is cut out along a flat surface so as not to interfere with the first engaging part 404A.

According to such an overtube 300, the distal end of the endoscope insertion part 102 and the distal end of the treatment tool insertion part 202 through which the overtube 300 is inserted can be spaced apart from each other even in a case where the spacing between the endoscope insertion passage 306 and the treatment tool insertion passage 308 in the overtube 300 is narrowed for reduction in diameter. Therefore, there is an advantage that the state of the distal end (treatment part 206) of the treatment tool 200 with an endoscope 100 is easily observed.

EXPLANATION OF REFERENCES

10: endoscopic surgical device
100: endoscope
102: endoscope insertion part
200: treatment tool
202: treatment tool insertion part
300: overtube
300a: reference axis
302: proximal end surface
304: distal end surface
306: endoscope insertion passage
306a: endoscope insertion axis
308: treatment tool insertion passage
308a: treatment tool insertion axis
310: first proximal end opening
312: first distal end opening
314: second proximal end opening
316: second distal end opening
320: long tubular overtube part
322: long tubular body
324: partition wall member
326: endoscope guide groove
328: treatment tool guide groove
340: proximal end cap
360: distal end cap
400: slider 402: coupling ring
404: ring part
404A: first engaging part
406: aim part
408: rear restriction end
410: front restriction end
412: engagement hole
420: endoscope coupling part
422: treatment tool coupling part
430: endoscope fixing tool
432, 452: frame
434, 454: pressure-contact member
436: protrusion
450: treatment tool fixing tool
500: sheathing tube

What is claimed is:

1. An endoscopic surgical device comprising:
a first medical instrument having a first insertion part inserted into a body cavity;
a second medical instrument having a second insertion part inserted into the body cavity; and
an overtube that passes through a body wall, is inserted into the body cavity, and guides the first insertion part and the second insertion part into the body cavity,
wherein the overtube includes
an overtube body having a distal end, a proximal end, and a longitudinal axis,
a first distal end opening and a second distal end opening provided at the distal end of the overtube body,
a first proximal end opening and a second proximal end opening provided at the proximal end of the overtube body,
a first insertion passage that is provided along the longitudinal axis of the overtube body, allows the first distal end opening and the first proximal end opening to communicate with each other, and allows the first insertion part to be inserted therethrough so as to be movable forward and backward,
a second insertion passage that is provided along the longitudinal axis of the overtube body, allows the second distal end opening and the second proximal end opening to communicate with each other, and allows the second insertion part to be inserted therethrough so as to be movable forward and backward, and
a coupling mechanism that has a first coupling part coupled to the first insertion part inserted through the first insertion passage and a second coupling part coupled to the second insertion part inserted through the second insertion passage, and
wherein the coupling mechanism dudes
a partition wall member that is housed inside the overtube body and extends along the longitudinal axis and that forms a portion of the first insertion passage and a portion of the second insertion passage,
a first fixing tool that has the first coupling part and is movable forward and backward along the first insertion passage,
a second fixing tool that has the second coupling part and is movable forward and backward along the second insertion passage, and
a driving member that is movable forward and backward along the longitudinal axis with respect to the partition wall member and that has an interlocking region where either the first fixing tool or the second fixing tool is moved forward and backward in an interlocking manner with the forward and backward movement of the other of the first fixing tool and the second fixing tool, wherein the driving member has a first engaging part engaged with a protrusion of the first fixing tool protruding from an outer peripheral surface of the first fixing tool.

2. The endoscopic surgical device according to claim 1, wherein the driving member further has a non-interlocking region where either the first fixing tool or the second fixing tool is not moved forward and backward with the forward and backward movement of the other of the first fixing tool and the second fixing tool.

3. The endoscopic surgical device according to claim 1, wherein the driving member has a second engaging part engaged with the second fixing tool,
wherein the first engaging part has a first restricting part that restricts the forward and backward movement of the first fixing tool in a first range, and
wherein the second engaging part has a second restricting part that restricts the forward and backward movement of the second fixing tool in a second range different from the first range.

4. The endoscopic surgical device according to claim 1, wherein the driving member has a second engaging part engaged with the second fixing tool, and
wherein at least one of the first engaging part or the second engaging part allows the movement of a corresponding fixing tool in a direction along with the longitudinal axis.

5. The endoscopic surgical device according to claim 1, wherein the driving member has a second engaging part engaged with the second fixing tool, and
wherein at least one of the first engaging part or the second engaging part allows the rotation of a corresponding fixing tool in a direction around an axis.

6. The endoscopic surgical device according to claim 1, wherein the partition wall member has a first guide groove that constitutes the portion of the first insertion passage, and a second guide groove that constitutes the portion of the second insertion passage.

7. The endoscopic surgical device according to claim 1, wherein the first insertion passage and the second insertion passage are disposed parallel to each other.

8. The endoscopic surgical device according to claim 1, wherein the first insertion passage and the second insertion passage are disposed to obliquely intersect each other.

9. The endoscopic surgical device according to claim 1, wherein the first medical instrument is an endoscope in which an observation part is provided at a distal end of the first insertion part, and
wherein the second medical instrument is a treatment tool in which a treatment part is provided at a distal end of the second insertion part.

10. The endoscopic surgical device according to claim 8, wherein the first medical instrument is an endoscope in which an observation part is provided at a distal end of the first insertion part,
wherein the second medical instrument is a treatment tool in which a treatment part is provided at a distal end of the second insertion part,
wherein the first insertion passage is disposed to obliquely intersect the longitudinal axis of the overtube body, and
wherein the second insertion passage is disposed parallel to the longitudinal axis of the overtube body.

11. An overtube comprising:
- an overtube body having a distal end, a proximal end, and a longitudinal axis;
- a first distal end opening and a second distal end opening provided at a distal end of the overtube body;
- a first proximal end opening and a second proximal end opening provided at a proximal end of the overtube body;
- a first insertion passage that is provided along the longitudinal axis of the overtube body, allows the first distal end opening and the first proximal end opening to communicate with each other, and allows a first insertion part of a first medical instrument to be inserted therethrough so as to be movable forward and backward;
- a second insertion passage that is provided along the longitudinal axis of the overtube body, allows the second distal end opening and the second proximal end opening to communicate with each other, and allows a second insertion part of a second medical instrument to be inserted therethrough so as to be movable forward and backward; and
- a coupling mechanism that has a first coupling part coupled to the first insertion part inserted through the first insertion passage and a second coupling part coupled to the second insertion part inserted through the second insertion passage, wherein the coupling mechanism includes
- a partition wall member that is housed inside the overtube body and extends along the longitudinal axis and that forms a portion of the first insertion passage and a portion of the second insertion passage,
- a first fixing tool that has the first coupling part and is movable forward and backward along the first insertion passage,
- a second fixing tool that has the second coupling part and is movable forward and backward along the second insertion passage, and
- a driving member that is movable forward and backward along the longitudinal axis with respect to the partition wall member and that has an interlocking region where either the first fixing tool or the second fixing tool is moved forward and backward in an interlocking manner with the forward and backward movement of the other of the first fixing tool and the second fixing tool, wherein the driving member has a first engaging part engaged with a protrusion of the first fixing tool protruding from an outer peripheral surface of the first fixing tool.

* * * * *